United States Patent

Bouchard et al.

[11] Patent Number: 5,728,849
[45] Date of Patent: Mar. 17, 1998

[54] TAXOIDS THEIR PREPARATION AND PHARMACEUTICAL COMPOSITIONS CONTAINING THEM

[75] Inventors: Hervé Bouchard, Thiais; Alain Commerçon, Vitry-sur-Seine, both of France

[73] Assignee: Rhone-Poulenc Rorer S.A., Antony, France

[21] Appl. No.: 771,751

[22] Filed: Dec. 20, 1996

[30] Foreign Application Priority Data

Dec. 22, 1995 [FR] France .................. 95 15379

[51] Int. Cl.$^6$ .............. C07D 305/14; C07D 307/93; A61K 31/34; A61K 31/335
[52] U.S. Cl. .............. 549/456; 549/510; 549/511; 514/449; 514/468
[58] Field of Search .............. 549/456, 510, 549/511; 514/468, 449

[56] References Cited

U.S. PATENT DOCUMENTS 5,254,580 10/1993 Chen et al. .............. 514/449

*Primary Examiner*—Ba K. Trinh
*Attorney, Agent, or Firm*—Finnegan, Henderson, Farabow, Garrett & Dunner, L.L.P.

[57] ABSTRACT

New taxoids of general formula (I):

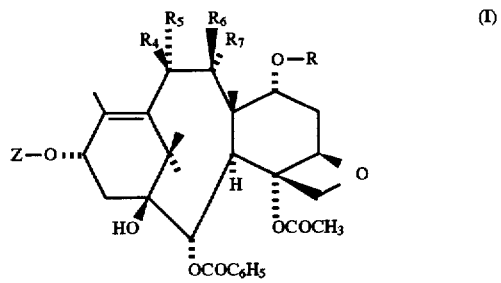

wherein

Z represents a hydrogen atom or a radical of general formula:

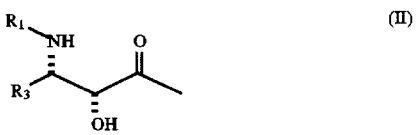

in which $R_1$ represents an optionally substituted benzoyl radical, a thenoyl or furoyl radical or a radical $R_2$—O—CO— in which $R_2$ represents an alkyl, alkenyl, alkynyl, cycloalkyl, cycloalkenyl, bicycloalkyl or phenyl radical, optionally substituted, or a heterocyclic radical, $R_3$ represents an alkyl, alkenyl, alkynyl, cycloalkyl, cycloalkenyl, phenyl, naphthyl or aromatic heterocyclic radical, either $R_4$ represents a hydrogen atom, $R_6$ and $R_7$ together form a ketone function, and $R$ and $R_5$ together form a bond, or $R_4$ represents a hydrogen atom or a hydroxyl radical or an alkoxy, alkenyloxy or alkynyloxy radical, optionally substituted, an alkanoyloxy, aryloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy or dialkylcarbamoyloxy radical, $R_5$ represents a hydrogen atom, or $R_4$ and $R_5$ together form a ketone function $R_6$ represents a hydrogen atom, and $R$ and $R_7$ together form a bond.

The new products of general formula (I) in which Z represents a radical of general formula (II) display noteworthy antitumour and antileukaemic properties.

16 Claims, No Drawings

TAXOIDS THEIR PREPARATION AND PHARMACEUTICAL COMPOSITIONS CONTAINING THEM

The present invention relates to new taxoids of general formula:

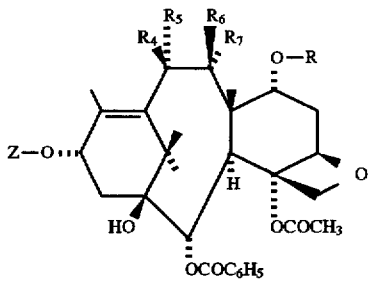

in which:

Z represents a hydrogen atom or a radical of general formula:

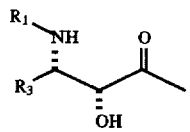

in which:

$R_1$ represents a benzoyl radical optionally substituted with one or more identical or different atoms or radicals chosen from halogen atoms and alkyl radicals containing 1 to 4 carbon atoms, alkoxy radicals containing 1 to 4 carbon atoms or trifluoromethyl radicals, a thenoyl or furoyl radical or a radical $R_2$—O—CO— in which $R_2$ represents an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, cycloalkenyl radicals containing 4 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hereto atoms chosen from nitrogen, oxygen and sulphur atoms and optionally substituted with one or more identical or different substituents chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, on the understanding that, in the substituents of the phenyl, α- or β-naphthyl and aromatic heterocyclic radicals, the alkyl radicals and the alkyl portions of the other radicals contain 1 to 4 carbon atoms, and that the alkenyl and alkynyl radicals contain 2 to 8 carbon atoms, and that the aryl radicals are phenyl or α- or β-naphthyl radicals, either $R_4$ represents a hydrogen atom, $R_6$ and $R_7$ together form a ketone function, and R and $R_5$ together form a bond, or $R_4$ represents a hydrogen atom or a hydroxyl radical or an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms, a cycloalkenyloxy radical containing 3 to 6 carbon atoms, an alkanoyloxy radical in which the alkanoyl portion contains 1 to 6 carbon atoms in an unbranched or branched chain, an aroyloxy radical in which the aryl portion contains 6 to 10 carbon atoms, an alkenoyloxy radical in which the alkenoyl portion contains 3 to 6 carbon atoms in an unbranched or branched chain, an alkynoyloxy radical in which the alkynoyl portion contains 3 to 6 carbon atoms in an unbranched or branched chain, a cycloalkanoyloxy radical containing 3 to 6 carbon atoms, an alkoxyacetyl radical in which the alkyl portion contains 1 to 6 carbon atoms in an unbranched or branched chain, an alkylthioacetyl radical in which the alkyl portion contains 1 to 6 carbon atoms in an unbranched or branched chain or an alkyloxycarbonyloxy radical in which the alkyl portion contains 1 to 6 carbon atoms in an unbranched or branched chain, these radicals being optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms, optionally substituted with an alkyl radical containing 1 to 4 carbon atoms or a phenyl radical or a phenylalkyl radical in which the alkyl portion contains 1 to 4 carbon atoms, or alternatively $R_4$ represents a carbamoyloxy or alkylcarbamoyloxy radical in which the alkyl portion contains 1 to 4 carbon atoms, a dialkylcarbamoyloxy radical in which each alkyl portion contains 1 to 4 carbon atoms or a benzoyloxy radical or a heterocyclylcarbonyloxy radical in which radical the heterocyclic portion represents a 5- or 6-membered aromatic heterocycle containing one or more hetero atoms chosen from oxygen, sulphur and nitrogen atoms, $R_5$ represents a hydrogen atom or $R_4$ and $R_5$ together form a ketone function, $R_6$ represents a hydrogen atom, and R and $R_7$ together form a bond.

Preferably, the aryl radicals which can be represented by $R_3$ are phenyl or α- or β-naphthyl radicals optionally substituted with one or more atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by $R_3$ are 5-membered aromatic heterocyclic radicals containing one or more identical or different atoms chosen from nitrogen, oxygen and sulphur atoms, optionally substituted with one or more identical or different substituents chosen from halogen atoms (fluorine, chlorine, bromine, iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano, carboxyl or carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

More especially, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals chosen from halogen atoms (fluorine, chlorine) and alkyl (methyl), alkoxy (methoxy), dialkylamino (dimethylamino), acylamino (acetylamino), alkoxycarbonylamino (tertbutoxycarbonylamino) or trifluoromethyl radicals, or a 2- or 3-furyl, 2- or 3-thienyl or 2-, 4- or 5-thiazolyl radical, and either $R_4$ represents a hydrogen atom, $R_6$ and $R_7$ together form a ketone function and R and $R_5$ together form a bond, or $R_4$ represents a hydroxyl radical or an alkoxy radical containing 1 to 6 carbon atoms, an alkanoyloxy radical containing 1 to 6 carbon atoms or an alkoxyacetyl radical in which the alkyl portion contains 1 to 6 carbon atoms, $R_5$ represents a hydrogen atom, $R_6$ represents a hydrogen atom and R and $R_7$ together form a bond, or $R_4$ and $R_5$ together form a ketone function, $R_6$ represents a hydrogen atom, R and $R_7$ together form a bond.

Still more especially, the present invention relates to the products of general formula (I) in which Z represents a hydrogen atom or a radical of general formula (II) in which $R_1$ represents a benzoyl radical or a radical $R_2$—O—CO— in which $R_2$ represents a tertbutyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, either $R_4$ represents a hydrogen atom, $R_6$ and $R_7$ together form a ketone function and R and $R_5$ together form a bond, or $R_4$ represents a hydroxyl radical or a methoxy, acetoxy or methoxyacetoxy radical, $R_5$ represents a hydrogen atom, $R_6$ represents a hydrogen atom and R and $R_7$ together form a bond.

The products of general formula (I) in which Z represents a radical of general formula (II) display noteworthy antitumour and antileukaemic properties.

According to the invention, the products of general formula (I) in which either $R_4$ represents a hydrogen atom, $R_6$ and $R_7$ together form a ketone function and R and $R_5$ together form a bond, or $R_4$ represents a hydroxyl radical, $R_5$ represents a hydrogen atom, $R_6$ represents a hydrogen atom and R and $R_7$ together form a bond may be obtained by the action of a reducing agent on a product of general formula

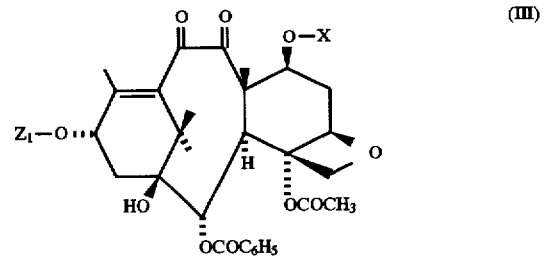
(III)

in which $Z_1$ represents a hydrogen atom or a group protecting the hydroxyl function or a radical of general formula:

(IV)

in which $R_1$ and $R_3$ are defined as above, and $R_8$ represents a group protecting the hydroxyl function, and X represents, with the oxygen atom to which it is linked, a leaving group chosen from alkylsulphonyl radicals containing 1 to 4 carbon atoms optionally substituted with one or more halogen atoms, or arylsulphonyl radicals in which the aryl portion is a phenyl radical optionally substituted with one or more identical or different atoms or radicals chosen from halogen atoms and alkyl radicals containing 1 to 4 carbon atoms, or nitro or trifluoromethyl radicals, to obtain a product of general formula:

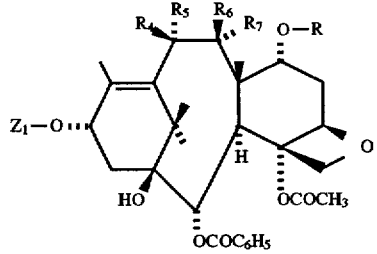

(V)

in which $Z_1$, R, $R_4$, $R_5$, $R_6$ and $R_7$ are defined as above, followed by the replacement of the protective group represented by $Z_1$ or $R_8$ by a hydrogen atom.

Generally, the reducing agent is chosen from aluminohydrides or borohydrides such as alkali or alkaline-earth metal borohydrides, such as sodium borohydride, in the presence of an aliphatic alcohol containing 1 to 4 carbon atoms such as ethanol, the reaction being carried out at a temperature of between 0° and 50° C., preferably in the region of 20° C.

Preferably, the protective group represented by $R_8$ is chosen from groups which can be easily introduced and easily removed without affecting the rest of the molecule, such as silylated radicals such as the triethylsilyl radical. The replacement of the protective group by a hydrogen atom, when it represents a silylated radical, is generally performed by means of an inorganic acid such as hydrochloric acid in an aliphatic alcohol containing 1 to 4 carbon atoms, at a temperature of between −10° and 20° C., preferably in the region of 0° C., or in the presence of a source of fluoride ions such as a hydrofluoric acid-triethylamine complex, working in an inert organic solvent such as a halogenated aliphatic hydrocarbon such as dichloromethane at a temperature of between 0° and 50° C., preferably in the region of 20° C.

The carrying out of the process generally leads to a mixture of a product of general formula (I) in which $R_4$ represents a hydrogen atom, $R_6$ and $R_7$ together form a ketone function, and R and $R_5$ together form a bond, and of a product of general formula (I) in which $R_4$ represents a hydroxyl radical, $R_5$ represents a hydrogen atom, $R_6$ represents a hydrogen atom and R and $R_7$ together form a bond, which are separated by the usual methods such as chromatography.

The product of general formula (III) may be obtained by the action of an oxidizing agent on a product of general formula:

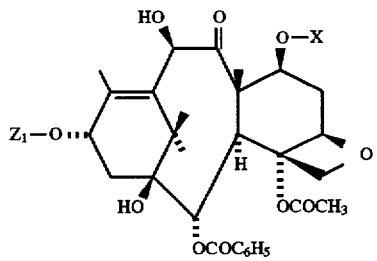

(VI)

in which $Z_1$ and X are defined as above.

Generally, the oxidizing agent is chosen from agents which make it possible to oxidize the secondary alcohol function without affecting the rest of the molecule, such as for example oxygen, ammonium peruthenate, manganese dioxide, copper acetate or pyridinium chlorochromate. Preferably, pyridinium chlorochromate is used, working in an organic solvent such as optionally halogenated aliphatic hydrocarbons such as dichloromethane, at a temperature of between 0° and 50° C., preferably in the region of 25° C.

The product of general formula (VI) in which $Z_1$ and X are defined as above may be obtained by the action of a sulphonyl halide on a product of general formula:

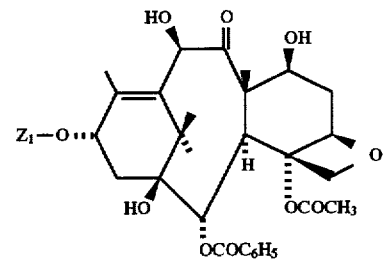

(VII)

in which $Z_1$ is defined as above.

The product of general formula (VI) in which X preferably represents a trifluoromethylsulphonyl radical may be obtained by the action of a derivative of trifluoromethanesulphonic acid such as the anhydride or N-phenyl trifluoromethanesulphonimide in an inert organic solvent such as an optionally halogenated aliphatic hydrocarbon such as dichloromethane, working in the presence of an organic base such as pyridine or a tertiary aliphatic amine such as triethylamine, at a temperature of between −50° and 20° C., on a product of general formula (VII).

The product of general formula (VII) in which $Z_1$ represents a radical of general formula (IV), in which $R_8$ is defined as above, may be obtained by the action of a silylating agent on a product of general formula:

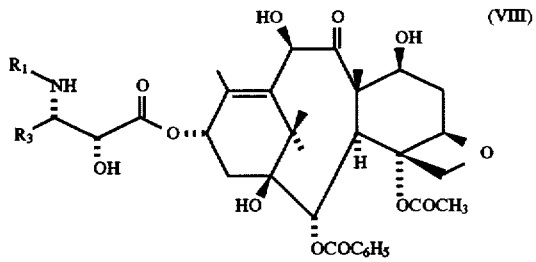

(VIII)

in which $R_1$ and $R_3$ are defined as above.

Generally, a trialkylsilyl halide such as triethylsilyl chloride is used, working in an optionally halogenated hydrocarbon such as dichloromethane, in the presence of an organic base such as pyridine or a tertiary aliphatic amine such as triethylamine.

The product of general formula (VIII) for which $R_3$ represents a phenyl radical and $R_1$ represents a tert-butyl radical is known by the name of docetaxel. The docetaxel derivatives which correspond to the general formula (VIII) may be obtained under the conditions described in International Applications PCT WO 92/09589, WO 93/16060 and WO 94/12484 all hereby incorporated by reference.

The product of general formula (VII) in which $Z_1$ represents a hydrogen atom is 10-deactylbaccatin III which is extracted in a known manner from yew (Taxus baccata) leaves.

According to the invention, the products of general formula (I) in which Z is defined as above, $R_4$ represents an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms, a cycloalkenyloxy radical containing 3 to 6 carbon atoms, an alkanoyloxy radical in which the alkanoyl portion contains 1 to 6 carbon atoms in an unbranched or branched chain, an alkenoyloxy radical in which the alkenoyl portion contains 3 to 6 carbon atoms in an unbranched or branched chain, an alkynoyloxy radical in which the alkynoyl portion contains 3 to 6 carbon atoms in an unbranched or branched chain, a cycloalkanoyloxy radical containing 1 to 6 carbon atoms, an alkoxyacetyl radical in which the alkyl portion contains 1 to 6 carbon atoms in an unbranched or branched chain, an alkylthioacetyl radical in which the alkyl portion contains 1 to 6 carbon atoms in an unbranched or branched chain or an alkyloxycarbonyloxy radical in which the alkyl portion contains 1 to 6 carbon atoms in an unbranched or branched chain, these radicals being optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms, optionally substituted with an alkyl radical containing 1 to 4 carbon atoms or a phenyl radical or a phenylalkyl radical in which the alkyl portion contains 1 to 4 carbon atoms, or alternatively $R_4$ represents a carbamoyloxy or alkylcarbamoyloxy radical in which the alkyl portion contains 1 to 4 carbon atoms, a dialkylcarbamoyloxy radical in which each alkyl portion contains 1 to 4 carbon atoms or a benzoyloxy radical or a heterocyclic radical attached to a carbonyloxy group in which radical the heterocyclic portion represents a 5- or 6-membered aromatic heterocycle containing one or more hetero atoms chosen from oxygen, sulphur and nitrogen atoms, $R_5$ represents a hydrogen atom, $R_6$ represents a hydrogen atom, and R and $R_7$ together form a bond, may be obtained by the action of a product of general formula:

$$R'_4\text{---}Y \qquad (IX)$$

in which $R'_4$ is such that $R'_4$—O— is identical to $R_4$ defined as above and Y represents a leaving group such as a halogen atom, on the product of general formula (V) in which $Z_1$ is defined as above, $R_4$ represents a hydroxyl radical, $R_6$ represents a hydrogen atom and R and $R_7$ together form a bond.

Generally, the action of a product of general formula (IX) on the product of general formula (V) defined above is performed, after optional metalation of the hydroxyl function at position 10 by means of an alkali or alkaline-earth metal hydride such as sodium hydride, an alkali metal amide such as lithium diisopropylamide or an alkali metal alkylide such as n-butyllithium, working in an organic solvent such as dimethylformamide or tetrahydrofuran or pyridine, at a temperature of between 0° and 50° C., optionally followed by the replacement of the group protecting the hydroxyl function $Z_1$ or $R_8$ under the conditions described above.

When $Z_1$ is different from a radical of general formula (IV), it is particularly advantageous to perform the reaction on a product of general formula (V) in which $Z_1$ represents a group protecting the hydroxyl function which is preferably a triethylsilyl radical. In this case, the protective group is introduced by the action of a trialkylsilyl halide, preferably triethylsilyl chloride, on a product of general formula (VI) in which $Z_1$ represents a hydrogen atom.

According to the invention, the products of general formula (I) in which Z represents a radical of general formula (II), $R_4$ and $R_5$ together form a ketone function, $R_6$ represents a hydrogen atom, and R and $R_7$ together form a bond, may be obtained by oxidation of a product of general formula (V) in which $Z_1$ is defined as above, $R_4$ represents a hydroxyl radical, $R_5$ represents a hydrogen atom, $R_6$ represents a hydrogen atom and R and $R_7$ together form a bond, optionally followed by the replacement of the protective group represented by $Z_1$ or $R_8$ by a hydrogen atom under the conditions described above.

Generally, the oxidation is performed under the conditions described above for the oxidation of a product of general formula (VI).

According to the invention, the products of general formula (I) in which Z represents a radical of general formula (II), $R_4$, $R_5$ and $R_6$ each represent a hydrogen atom and R and $R_7$ together form a bond, may be obtained from a product of general formula (V) in which $Z_1$ is defined as above, $R_4$ represents a hydroxyl radical, $R_5$ and $R_6$ each represent a hydrogen atom and R and $R_7$ together form a bond, after conversion of the hydroxyl radical represented by $R_4$ to a dithiocarbonate followed by the reduction of the product obtained by means of a trialkyltin hydride such as tributyltin hydride, optionally followed by the replacement of the protective group represented by $Z_1$ or $R_8$ by a hydrogen atom under the conditions described above.

According to the invention, the products of general formula (I) may also be obtained by esterification of a product of general formula (I) in which $R_4$, $R_5$, $R_6$ and $R_7$ are defined as above, and Z represents a hydrogen atom by means of an acid of general formula:

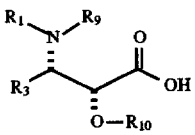
(X)

in which, either $R_9$ represents a hydrogen atom and $R_{10}$ represents a group protecting the hydroxyl function, or $R_9$ and $R_{10}$ together form a saturated 5- or 6-membered heterocycle, or by means of a derivative of this acid, followed by the replacement of the protective groups by hydrogen atoms.

The conditions for esterification and replacement of the protective groups are identical to those which are described, for example, in International Applications PCT WO 92/09589, WO 93/16060 and WO 94/12484.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M. L. Shelanski et al., Proc. Natl. Acad. Sci. USA, 70, 765–768 (1973). Study of the depolymerization of microtubules to tubulin is performed according to the method of G. Chauvière et al., C. R. Acad. Sci., 293, series II, 501–503 (1981). In this study, the products of general formula (I) in which Z represents a radical of general formula (II) were shown to be at least as active as Taxol and Taxotere.

In vivo, the products of general formula (I) in which Z represents a radical of general formula (II) were shown to be active in mice grafted with B16 melanoma at doses of between 1 and 10 mg/kg administered intraperitoneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which expresses mdr 1.

The examples which follow illustrate the present invention.

EXAMPLE 1

117 mg of sodium borohydride are added to a solution of 0.65 g of 4α-acetoxy-2α-benzoyloxy-5β,20-epoxy-1β-hydroxy-9,10-dioxo-7β-trifluoromethanesulphonyloxy-11-taxen-13α-yl (2R,3S)-3-tert-butoxycarbonylamino-3-phenyl-2-triethylsilyloxypropionate in 6.5 cm$^3$ of absolute ethanol maintained under an argon atmosphere at a temperature in the region of 20° C. After 5 minutes at a temperature in the region of 20° C., the reaction mixture is diluted with 50 cm$^3$ of ethyl acetate. The organic phase is washed with 3 times 10 cm$^3$ of distilled water and then with twice 10 cm$^3$ of a saturated aqueous sodium chloride solution, dried over magnesium sulphate, filtered through sintered glass and concentrated under reduced pressure (2.7 kPa) at a temperature in the region of 40° C. 600 mg of a white foam are thereby obtained which are combined with 313 mg of an identical crude mixture obtained from 500 mg of 4α-acetoxy-2α-benzoyloxy-5β,20-epoxy-1β-hydroxy-9,10-dioxo-7β-trifluoromethanesulphonyloxy-11-taxen-13α-yl (2R,3S)-3-tert-butoxycarbonylamino-3-phenyl-2-triethylsilyloxypropionate under the same conditions. The purification is performed by chromatography at atmospheric pressure on 100 g of silica (0.063–0.2 mm) contained in a column 3.5 cm in diameter, eluting with an ethyl acetate/dichloromethane mixture (elution gradient from 2–98 to 15–85 by volume), collecting 20-cm$^3$ fractions. The fractions containing only the desired products are pooled and concentrated to dryness under reduced pressure (2.7 kPa) at 40° C. for 2 hours. 153 mg of 4α-acetoxy-2α-benzoyloxy-5β,20-epoxy-1β-hydroxy-7α,10α-epoxy-9-oxo-11-taxen-13α-yl (2R,3S)-3-tert-butoxycarbonylamino-3-phenyl-2-triethylsilyloxypropionate are thereby obtained in the form of a white foam and 384 mg of 4α-acetoxy-2α-benzoyloxy-5β,20-epoxy-1β,10β-dihydroxy-7α,9α-epoxy-11-taxen-13α-yl (2R,3S)-3-tert-butoxycarbonylamino-3-phenyl-2-triethylsilyloxypropionate in the form of a white foam.

4α-Acetoxy-2α-benzoyloxy-5β,20- epoxy-1β-hydroxy-7α,10α-epoxy-9-oxo-11-taxen-13α-yl (2R,3S)-3-tert-butoxycarbonylamino-3-phenyl-2-triethylsilyloxypropionate displays the following characteristics:

$^1$H NMR spectrum (400 MHz; CDCl$_3$; δ in ppm; coupling constants J in Hz): 0.34 and 0.41 (2 mts, 6H: CH$_2$ of the triethylsilyl at position 2'); 0.77 (t, J=7.5, 9H: CH$_3$ of the triethylsilyl at position 2'); 1.23 (s, 3H: CH$_3$); 1.38 (s, 3H: CH$_3$); 1.40 (s, 9H: C(CH$_3$)$_3$); 1.82 (s, 3H: CH$_3$); 1.90 (s, 3H: CH$_3$); 1.93 (s, 1H: OH at position 1); from 2.15 to 2.40 (mt, 2H: CH$_2$ at position 14); from 2.15 to 2.40 and 2.48 (2 mts, 1H each: CH$_2$ in position 6); 2.48 (s, 3H: COCH$_3$); 3.70 (d, J=8, 1H: H at position 7); 4.25 and 4.32 (2 d, J=8, 1H each: CH$_2$ at position 20); 4.58 (d, J=7, 1H: H at position 3); 4.59 (broad s, 1H: H at position 2'); 4.86 (mt, 1H: H at position 10); 5.11 (d, J=5, 1H: H at position 5); 5.32 (broad d, J=10, 1H: H at position 3'); 5.56 (d, J=10, 1H: CONH); 5.62 (d, J=7, 1H: H at position 2); 6.34 (broad t, J=9, 1H: H [lacuna]; from 7.25 to 7.45 (mt, 5H: aromatic H at position 3'); 7.50 (t, J=7.5, 2H: OCOC$_6$H$_5$ H at the meta position); 7.62 (t, J=7.5, 1H: OCOC$_6$H$_5$ H at the para position); 8.13 (d, J=7.5, 2H: OCOC$_6$H$_5$ H at the ortho position).

4α-Acetoxy-2α-benzoyloxy-5β,20-epoxy-1β,10β-dihydroxy-7α,9α-epoxy-11-taxen-13α-yl (2R,3S)-3-tert-butoxycarbonylamino-3-phenyl-2-triethylsilyloxypropionate displays the following characteristics:

$^1$H NMR spectrum (400 MHz; CDCl$_3$; δ ppm; coupling constants J in Hz): 0.33 and 0.40 (2 mts, 6H: CH$_2$ of the triethylsilyl at position 2'); 0.75 (t, J=7.5, 9H: CH$_3$ of the triethylsilyl at position 2'); 1.13 (s, 3H: CH$_3$); 1.27 (s, 3H: CH$_3$); 1.37 (s, 9H: C(CH$_3$)$_3$); 1.75 (s, 3H: CH$_3$); 2.23 and from 2.30 to 2.50 (dd and mt respectively, J=15 and 8, 1H each: CH$_2$ at position 14); from 2.30 to 2.50 (mt, 2H: CH$_2$ at position 6) 2.48 (s, 3H: COCH$_3$); 2.55 (d, J=7, 1H: OH at position 10); 4.05 and 4.29 (2 d, J=7.5, 1H each: CH$_2$ at position 20); 4.17 (d, J=6, 1H: H at position 3); 4.60 (broad s, 1H: H at position 2'); from 4.75 to 4.90 (mt, 3H: H at position 7-H at position 9 and H at position 10); 4.97 (broad s, 1H: H at position 5); 5.33 (broad d, J=10, 1H: H at position 3'); 5.54 (d, J=10, 1H: CONH); 5.80 (d, J=6, 1H: H at position 2); 6.18 (broad t, J=8, 1H: H at position 13); from 7.25 to 7.45 (mt, 5H: aromatic H at position 3'); 7.49 (t, J=7.5, 2H: OCOC$_6$H$_5$ H at the meta position); 7.62 (t, J=7.5, 1H: OCOC$_6$H$_5$ H at the para position); 8.15 (d, J=7.5, 2H: OCOC$_6$H$_5$ H at the ortho position).

A solution of 126 mg of 4α-acetoxy-2α-benzoyloxy-5β,20-epoxy-1β,10β-dihydroxy-7α,9α-epoxy-11-taxen-13α-yl (2R,3S)-3-tert-butoxycarbonylamino-3-phenyl-2-triethylsilyloxypropionate in 1.7 cm$^3$ of 0.1N ethanolic solution of hydrogen chloride is stirred, under an argon atmosphere, at a temperature in the region of 0° C., for 1 hour. The reaction mixture is then diluted with 20 cm$^3$ of dichloromethane. The organic phase is washed with twice 5 cm$^3$ of distilled water and then with twice 5 cm$^3$ of a saturated aqueous sodium chloride solution, dried over magnesium sulphate, filtered through sintered glass and concentrated under reduced pressure (2.7 kPa) at a temperature in the region of 40° C. 130 mg of an ivory-coloured foam are thereby obtained, which product is purified by preparative thin-layer chromatography [12 Merck preparative silica gel 60F$_{254}$ plates: 20×20 cm; thickness 0.25 mm; application in solution in dichloromethane], eluting twice with a methanol/dichloromethane (5–95 by volume) mixture. After elution of the zone corresponding to the desired product with a methanol/dichloromethane (15–85 by volume) mixture, filtration through sintered glass and then evaporation of the solvent under reduced pressure (2.7 kPa) at a temperature in the region of 40° C., 22.6 mg of 4α-acetoxy-2α-benzoyloxy-5β,20-epoxy-1β,10β-dihydroxy-7α,9α-epoxy-11-taxen-13α-yl (2R,3S)-3-tert-butoxycarbonylamino-3-phenyl-2-hydroxypropionate are obtained in the form of a white foam, the characteristics of which are as follows:

$^1$H NMR spectrum (400 MHz; CDCl$_3$; at a temperature of 333° K, δ in ppm; coupling constants J in Hz): 1.14 (s, 3H: CH$_3$); 1.25 (s, 3H: CH$_3$); 1.40 (s, 9H: C(CH$_3$)$_3$); 1.74 (s, 3H: CH$_3$); 1.86 (s, 1H: OH at position 1); 1.95 (s, 3H: CH$_3$); from 2.14 to 2.45 (mt, 4H: CH$_2$ at position 14 and CH$_2$ at position 6); 2.33 (s, 3H: COCH$_3$); 2.50 (unres. comp., 1H: OH at position 10); 3.67 (unres. comp.,1H: OH at position 2'); 4.06 and 4.27 (2 d, J=7.5, 1H each: CH$_2$ at position 20); 4.17 (d, J=6, 1H: H at position 3); 4.65 (mt, 1H: H at position 2'); from 4.75 to 4.90 (mt, 3H: H at position 7-H at position 9 and H at position 10); 4.93 (broad s, 1H: H at position 5);

5.30 (broad d, J=10, 1H: H at position 3'); 5.50 (d, J=10, 1H: CONH); 5.79 (d, J=6, 1H: H at position 2); 6.06 (broad t, J=9, 1H: H at position 13); 7.30 (t, J=7.5, 1H: H at the para position of the aromatic at position 3'); 7.38 (t, J=7.5, 2H: H at the meta position of the aromatic at position 3'); 7.44 (d, J=7, 2H: H at the ortho position of the aromatic at position 3'); 7.49 (t, J=7.5, 2H: OCOC$_6$H$_5$ H at the meta position); 7.61 (t, J=7.5, 1H: OCOC$_6$H$_5$ H at the para position); 8.13 (d, J=7.5, 2H: OCOC$_6$H$_5$ H at the ortho position).

4α-Acetoxy-2α-benzoyloxy-5β,20-epoxy-1β-hydroxy-9,10-dioxo-7β-trifluoromethanesulphonyloxy-11-taxen-13α-yl (2R,3S)-3-tert-butoxycarbonylamino-3-phenyl-2-triethylsilyloxypropionate may be prepared in the following manner:

1.91 g of pyridinium chlorochromate are rapidly added to a suspension of 1.87 g of 4α-acetoxy-2α-benzoyloxy-5β,20-epoxy-1β,10β-dihydroxy-9-oxo-7β-trifluoromethanesulphonyloxy-11-taxen-13α-yl (2R,3S)-3-tert-butoxycarbonylamino-3-phenyl-2-triethylsilyloxypropionate and 4 g of activated 4 Å molecular sieve in 10 cm$^3$ of anhydrous dichloromethane maintained under an argon atmosphere at a temperature in the region of 20° C. The reaction mixture is stirred for 20 hours at a temperature in the region of 20° C. and then purified directly by applying to a chromatography column at atmospheric pressure containing 200 g of silica (0.063–0.2 mm; column 3.5 cm in diameter), eluting with dichloromethane alone and then with a methanol/dichloromethane (0.5–99.5 by volume) mixture, collecting 15 cm$^3$ fractions. The fractions containing only the desired product are pooled and concentrated to dryness under reduced pressure (2.7 kPa) at 40° C. for 2 hours. 1.16 g of 4α-acetoxy-2α-benzoyloxy-5β,20-epoxy-1β-hydroxy-9,10-dioxo-7β-trifluoromethanesulphonyloxy-11-taxen-13α-yl (2R,3S)-3-tert-butoxy-carbonylamino-3-phenyl-2-triethylsilyloxypropionate are thereby obtained in the form of a pale yellow foam, the characteristics of which are as follows:

$^1$H NMR spectrum (400 MHz; CDCl$_3$; δ in ppm; coupling constants J in Hz): 0.42 (mt, 6H: CH$_2$ from triethylsilyl at position 2'); 0.81 (t, J=7.5, 9H: CH$_3$ from triethylsilyl at position 2'); 1.26 (s, 3H: CH$_3$); 1.35 (s, 3H: CH$_3$); 1.37 (s, 9H: C(CH$_3$)$_3$); 1.93 (s, 3H: CH$_3$); 2.01 (s, 3H: CH$_3$); 2.23 and 2.43 (2 dd, J=15 and 9, 1H each: CH$_2$ at position 14); 2.36 and 2.89 (2 mt, 1H each: CH$_2$ at position 6); 2.57 (s, 3H: COCH$_3$); 3.82 (d, J=7, 1H: H at position 3); 4.23 and 4.42 (2d, J=8.5, 1H each: CH$_2$ at position 20); 4.58 (broad s, 1H: H at position 2'); 4.95 (broad d, J=9.5, 1H: H at position 5); 5.28 (dd, J=10 and 7.5, 1H: H at position 7); 5.30 (broad d, J=10, 1H: H at position 3'); 5.52 (d, J=10, 1H: CONH); 5.87 (d, J=7, 1H: H at position 2); 6.28 (broad t, J=9, 1H: H at position 13); from 7.25 to 7.45 (mt, 5H: aromatic H at position 3'); 7.55 (t, J=7.5, 2H: OCOC$_6$H$_5$ H at the meta position); 7.67 (t, J=7.5, 1H: OCOC$_6$H$_5$ H at the para position); 8.13 (d, J=7.5 Hz, 2H: OCOC$_6$H$_5$ H at the ortho position).

4α-Acetoxy-2α-benzoyloxy-5β,20-epoxy-1β,10β-dihydroxy-9-oxo-7β-trifluoromethanesulphonyloxy-11-taxen-13α-yl (2R,3S)-3-tert-butoxycarbonylamino-3-phenyl-2-triethylsilyloxypropionate may be prepared in the following manner:

A solution of 3.2 cm$^3$ of trifluoromethanesulphonic anhydride in 3 cm$^3$ of anhydrous dichloromethane is added dropwise to a suspension of 8.85 g of 4α-acetoxy-2α-benzoyloxy-5β,20-epoxy-1β,7β,10β-trihydroxy-9-oxo-11-taxen-13α-yl (2R,3S)-3-tert-butoxycarbonylamino-3-phenyl-2-triethylsilyloxypropionate and 2 g of activated 4 Å molecular sieve in 50 cm$^3$ of anhydrous dichloromethane and 3.9 cm$^3$ of anhydrous pyridine maintained under an argon atmosphere at a temperature in the region of -30° C. The reaction mixture is stirred for 5 minutes at -35° C. and then for 1 hour at a temperature in the region of 0° C. After cooling to a temperature in the region of -10° C., 6 cm$^3$ of distilled water are added. After filtration through a sintered glass lined with Celite, rinsing of the sintered glass with 20 cm$^3$ of an ethyl acetate/dichloromethane (50—50 by volume) mixture and decantation, the organic phase is washed with twice 10 cm$^3$ of distilled water, dried over magnesium sulphate, filtered through sintered glass and concentrated under reduced pressure (2.7 kPa) at a temperature in the region of 40° C. 11.3 g of an orange-coloured foam are thereby obtained, which product is purified by chromatography at atmospheric pressure on 800 g of silica (0.063–0.2 mm) contained in a column 7 cm in diameter, eluting with a methanol/dichloromethane (1–99 and then 2–98 by volume) mixture, collecting 60 cm$^3$ fractions. The fractions containing only the desired product are pooled and concentrated to dryness under reduced pressure (2.7 kPa) at 40° C. for 2 hours. 9.55 g of 4α-acetoxy-2α-benzoyloxy-5β,20-epoxy-1β,10β-dihydroxy-9-oxo-7β-trifluoromethanesulphonyloxy-11-taxen-13α-yl (2R,3S)-3-tert-butoxycarbonylamino-3-phenyl-2-triethylsilyloxypropionate are thereby obtained in the form of a mixture. This mixture is purified by chromatography at atmospheric pressure on 700 g of silica (0.063–0.2 mm) contained in a column 6 cm in diameter, eluting with dichloromethane alone and then with an ethyl acetate/dichloromethane (5–95 by volume) mixture, collecting 60 cm$^3$ fractions. The fractions containing only the desired product are pooled and concentrated to dryness under reduced pressure (0.27 kPa) at 40° C. for 2 hours. 4.09 g of 4α-acetoxy-2α-benzoyloxy-5β,20-epoxy-1β,10β-dihydroxy-9-oxo-7β-trifluoromethanesulphonyloxy-11-taxen-13α-yl (2R,3S)-3-tert-butoxycarbonylamino-3-phenyl-2-triethylsilyloxypropionate are thereby obtained in the form of a pale yellow foam, the characteristics of which are as follows:

$^1$H NMR spectrum (300 MHz; CDCl$_3$; δ in ppm; coupling constants J in Hz): 0.38 (mt, 6H: CH$_2$ of the triethylsilyl at position 2'); 0.79 (t, J=7.5, 9H: CH$_3$ of the triethylsilyl at position 2'); 1.14 (s, 3H: CH$_3$); 1.28 (s, 3H: CH$_3$); 1.38 (s, 9H: C(CH$_3$)$_3$); 1.74 (s, 1H: OH at position 1); 1.94 (s, 3H: CH$_3$); 1.98 (s, 3H: CH$_3$); 2.20 and 2.37 (2 dd, J=16 and 9, 1H each: CH$_2$ at position 14); from 2.25 to 2.40 and 2.84 (2 mt, 1H each: CH$_2$ at position 6); 2.55 (s, 3H: COCH$_3$); 4.02 (broad s, 1H: OH at position 10); 4.04 (d, J=7 Hz, 1H: H at position 3); 4.24 and 4.38 (2d, J=8.5, 1H each: CH$_2$ at position 20); 4.54 (broad s, 1H: H at position 2'); 4.96 (broad d, J=9.5, 1H: H at position 5); 5.28 (broad d, J=10, 1H: H at position 3'); 5.38 (broad s, 1H: H at position 10); 5.44 (dd, J=10 and 7.5, 1H: H at position 7); 5.52 (d, J=10, 1H: CONH); 5.74 (d, J=7, 1H: H at position 2); 6.34 (broad t, J=9, 1H: H at position 13); from 7.25 to 7.40 (mt, 5H: aromatic H at position 3'); 7.50 (t, J=7.5, 2H: OCOC$_6$H$_5$ H at the meta position); 7.63 (t, J=7.5, 1H: OCOC$_6$H$_5$ H at the para position); 8.12 (d, J=7.5, 2H: OCOC$_6$H$_5$ H at the ortho position).

4α-Acetoxy-2α-benzoyloxy-5β,20-epoxy-1β,7β,10β-trihydroxy-9-oxo-11-taxen-13α-yl (2R,3S)-3-tert-butoxycarbonylamino-3-phenyl-2-triethylsilyloxypropionate may be prepared in the following manner:

8.05 cm$^3$ of triethylsilyl chloride are added dropwise to a solution of 8.6 g of 4α-acetoxy-2α-benzoyloxy-5β,20- epoxy-1β,7β,10β-trihydroxy-9-oxo-11-taxen-13α-yl (2R,3S)-3-tert-butoxycarbonylamino-3-phenyl-2-hydroxypropionate in 40 cm³ of anhydrous dichloromethane and 8.6 cm³ of anhydrous pyridine at a temperature in the region of 20° C. under an inert argon atmosphere. The reaction mixture is stirred at a temperature in the region of 20° C. for 2 hours and then 300 cm³ of dichloromethane are added. The organic phase is washed with twice 50 cm³ of distilled water, 50 cm³ of a 0.1N aqueous hydrochloric acid solution, 50 cm³ of distilled water, and then 50 cm³ of a saturated aqueous sodium chloride solution, dried over magnesium sulphate, filtered through sintered glass and concentrated under reduced pressure (2.7 kPa) at a temperature in the region of 40° C. 14.2 g of a white foam are thereby obtained, which product is purified by chromatography at atmospheric pressure on 800 g of silica (0.063–0.2 mm) contained in a column 7 cm in diameter, eluting with a methanol/dichloromethane (2–98 by volume) mixture, collecting 30 cm³ fractions. The fractions containing only the desired product are pooled and concentrated to dryness under reduced pressure (2.7 kPa) at 40° C. for 2 hours. 8.85 of 4α-acetoxy-2α-benzoyloxy-5β,20-epoxy-1β,7β,10β-trihydroxy-9-oxo-11-taxen-13α-yl (2R,3S)-3-tert-butoxycarbonylamino-3-phenyl-2-triethylsilyloxypropionate are thereby obtained in the form of a white foam.

EXAMPLE 2

0.012 cm³ of acetic anhydride and then 13.5 mg of N,N'-dimethylamino-4-pyridine are added to a solution of 200 mg of 4α-acetoxy-2α-benzoyloxy-5β,20-epoxy-1β,10β-dihydroxy-7α,9α-epoxy-11-taxen-13α-yl (2R,3S)-3-tert-butoxycarbonylamino-3-phenyl-2-triethylsilyloxypropionate in 2 cm³ of anhydrous pyridine maintained under an argon atmosphere at a temperature in the region of 20° C. After 30 minutes at a temperature in the region of 20° C., the reaction mixture is diluted with 40 cm³ of ethyl acetate. The organic phase is washed with twice 6 cm³ of distilled water and then 6 cm³ of a saturated aqueous sodium chloride solution, dried over magnesium sulphate, filtered through sintered glass and concentrated under reduced pressure (2.7 kPa) at a temperature in the region of 40° C. 237.4 mg of a pale yellow foam are thereby obtained, which produce is purified by chromatography at atmospheric pressure on 20 g of silica (0.063–0.2 mm) contained in a column 2.5 cm in diameter, eluting with an ethyl acetate/dichloromethane (elution gradient from 2–98 to 10–90 by volume) mixture, collecting 10 cm³ fractions. The fractions containing only the desired product are pooled and concentrated to dryness under reduced pressure (2.7 kPa) at 40° C. for 2 hours. 184.8 mg of 4α,10α-diacetoxy-2α-benzoyloxy-5β,20-epoxy-1β-hydroxy-7α,9α-epoxy-11-taxen-13α-yl (2R,3S)-3-tert-butoxycarbonylamino-3-phenyl-2-triethylsilyloxypropionate are thereby obtained in the form of a white foam, the characteristics of which are as follows:

$^1$H NMR spectrum (400 MHz; CDCl$_3$; δ in ppm; coupling constants J in Hz): 0.34 and 0.40 (2 mt, 6H: CH$_2$ of the triethylsilyl at position 2'); 0.76 (t, J=7.5, 9H: CH$_3$ of the triethylsilyl at position 2'); 1.26 (s, 3H CH$_3$); 1.28 (s, 3H: CH$_3$); 1.38 (s, 9H: C(CH$_3$)$_3$); 1.72 (s, 3H: CH$_3$); 1.88 (s, 1H: OH at position 1); 2.01 (s, 3H: CH$_3$); 2.14 (s, 3H: COCH$_3$); 2.23 and from 2.30 to 2.45 (dd and mt respectively, J=15 and 9, 1H each: CH$_2$ at position 14); 2.39 (mt, 2H: CH$_2$ at position 6); 2.48 (s, 3H: COCH$_3$); 4.05 and 4.30 (2 d, J=7.5, 1H each: CH$_2$ at position 20); 4.13 (d, J=6, 1H: H at position 3); 4.62 (broad s, 1H: H at position 2'); 4.80 (t, J=7.5, 1H: H at position 7); 4.88 (d, J=6, 1H: H at position 9); 4.98 (broad s, 1H: H at position 5); 5.34 (broad d, J=10, 1H: H at position 3'); 5.54 (d, J=10, 1H: CONH); 5.71 (d, J=6, 1H: H at position 10); 5.83 (d, J=6, 1H: H at position 2); 6.10 (broad t, J=9, 1H: H at position 13); from 7.25 to 7.45 (mt, 5H: aromatic H at position 3'); 7.48 (t, J=7.5, 2H: OCOC$_6$H$_5$ H at the meta position); 7.62 (t, J=7.5, 1H: OCOC$_6$H$_5$ H at the para position); 8.15 (d, J=7.5, 2H: OCOC$_6$H$_5$ H at the ortho position).

0.93 cm³ of a hydrofluoric acid/triethylamine (3HF/Et$_3$N) complex is added dropwise to a solution of 180 mg of 4α,10β-diacetoxy-2α-benzoyloxy-5β,20-epoxy-1β-hydroxy-7α,9α-epoxy-11-taxen-13α-yl (2R,3S)-3-tert-butoxycarbonylamino-3-phenyl-2-triethylsilyloxypropionate in 1 cm³ of anhydrous dichloromethane maintained under an argon atmosphere at a temperature in the region of 20° C. After 7.5 hours at a temperature in the region of 20° C., the reaction mixture is diluted with 30 cm³ of ethyl acetate and 8 cm³ of a saturated aqueous sodium hydrogen carbonate solution. After decantation, the organic phase is washed with twice 8 cm³ of distilled water and then 8 cm³ of a saturated aqueous sodium chloride solution, dried over magnesium sulphate, filtered through sintered glass and concentrated under reduced pressure (2.7 kPa) at a temperature in the region of 40° C. 167.5 mg of a white foam are thereby obtained, which product is purified by preparative thin-layer chromatography on silica [9 Merck preparative silica gel 60F$_{254}$ plates; 20×20 thickness 0.5 mm; application in solution in dichloromethane], eluting with a methanol/dichloromethane (4–96 by volume) mixture. After elution of the zone corresponding to the desired product with a methanol/dichloromethane (15–85 by volume) mixture, filtration through sintered glass and then evaporation of the solvents under reduced pressure (2.7 kPa) at a temperature in the region of 40° C., 143.6 mg of 4α,10β-diacetoxy-2α-benzoyloxy-5β,20-epoxy-1β-hydroxy-7α,9α-epoxy-11-taxen-13α-yl (2R,3S)-3-tert-butoxycarbonylamino-3-phenyl-2-hydroxypropionate are obtained in the form of a white foam, the characteristics of which are as follows:

$^1$H NMR spectrum (400 MHz; CDCl$_3$; δ in ppm; coupling constants J in Hz): 1.24 ([lacuna]: CH$_3$); 1.32 (s, 3H: CH$_3$); 1.41 (s, 9H: C(CH$_3$)$_3$); 1.68 (s, 3H: CH$_3$); 1.91 (s, 1H: OH at position 1); 1.92 (s, 3H: CH$_3$); 2.12 (s, 3H: COCH$_3$); 2.21 and from 2.25 to 2.55 (dd and mt respectively, J=15 and 8, 1H each: CH$_2$ at position 14); from 2.25 to 2.55 (mt, 2H: CH$_2$ 6); 2.31 (s, 3H: COCH$_3$); 3.43 (unres. comp., 1H: OH at position 2'); 4.03 and 4.30 (2 d, J=8, 1H each: CH$_2$ at position 20); 4.13 (d, J=6, 1H: H at position 3); 4.65 (mt, 1H: H at position 2'); 4.82 (dd, J=8.5 and 5.5, 1H: H at position 7); 4.86 (d, J=6, 1H: H at position 9); 4.93 (broad s, 1H: H at position 5); 5.34 (broad d, J=10, 1H: H at position 3'); 5.54 (d, J=10, 1H: CONH); 5.65 (d, J=6, 1H: H at position 10); 5.83 (d, J=6, 1H: H at position 2); 6.03 (broad t, J=8, 1H: H at position 13); 7.30 (t, J=7.5, 1H: H at the para position of the aromatic at position 3'); 7.38 (t, J=7.5, 2H: H at the meta position of the aromatic at position 3'); 7.43 (d, J=7.5, 2H: H at the ortho position of the aromatic at position 3'); 7.50 (t, J=7.5, 2H: OCOC$_6$H$_5$ H at the meta position); 7.62 (t, J=7.5, 1H: OCOC$_6$H$_5$ H at the para position); 8.13 (d, J=7.5, 2H: OCOC$_6$H$_5$ H at the ortho position).

EXAMPLE 3

0.805 cm³ of hydrofluoric acid/triethylamine (3HF/Et$_3$N) complex is added dropwise to a solution of 149 mg of 4α-acetoxy-2α-benzoyloxy-5β,20-epoxy-1β-hydroxy-7α,10α-epoxy-9-oxo-11-taxen-13α-yl (2R,3S)-3-tert-butoxycarbonylamino-3-phenyl-2-triethylsilyloxypropionate, obtained in Example 1, in 1.5 cm³ of anhydrous dichloromethane, maintained under an argon atmosphere at a temperature in the region of 20° C. After 1 hour at a temperature in the region of 20° C., the reaction mixture is diluted with 50 cm³ of dichloromethane, 5 cm³ of a saturated aqueous sodium hydrogen carbonate solution and 5 cm³ of distilled water. After decantation, the organic phase is washed with 3 times 8 cm³ of distilled water and then 8 cm³ of a saturated aqueous sodium chloride solution, dried over magnesium sulphate, filtered through sintered glass and concentrated under reduced pressure (2.7 kPa) at a temperature in the region of 40° C. 133.2 mg of a pale yellow foam are thereby obtained, which product is purified by preparative thin-layer chromatography on silica [10 Merck preparative silica gel 60F$_{254}$ plates; 20×20 cm; thickness 0.5 mm; application in solution in dichloromethane), eluting with a methanol/dichloromethane (5–95 by volume) mixture. After elution of the zone corresponding to the desired product with a methanol/dichloromethane (15–85 by volume) mixture, filtration through sintered glass and then evaporation of the solvents under reduced pressure (2.7 kPa) at a temperature in the region of 40° C., 144.2 mg of 4α-acetoxy-2α-benzoyloxy-5β,20-epoxy-1β-hydroxy-7α,10α-epoxy-9-oxo-11-taxen-13α-yl (2R,3S)-3-tert-butoxycarbonylamino-3-phenyl-2-hydroxypropionate are obtained in the form of a white foam, which product is purified by preparative thin-layer chromatography on silica [8 Merck preparative silica gel 60F$_{254}$ plates; 20×20 cm; thickness 0.5 mm; application in solution in dichloromethane], eluting with a methanol/dichloromethane (2–98 by volume) mixture. After elution of the zone corresponding to the desired product with a methanol/dichloromethane (15–85 by volume) mixture, filtration through sintered glass and then evaporation of the solvents under reduced pressure (2.7 kPa) at a temperature in the region of 40° C., 92.8 mg of 4α-acetoxy-2α-benzoyloxy-5β,20-epoxy-1β-hydroxy-7α,10α-epoxy-9-oxo-11-taxen-13α-yl (2R,3S)-3-tert-butoxycarbonylamino-3-phenyl-2-hydroxypropionate are obtained in the form of a white foam, the characteristics of which are as follows:

¹H NMR spectrum (400 MHz; CDCl₃; at a temperature of 333° K, δ in ppm; coupling constants J in Hz): 1.23 (s, 3H: CH₃); 1.33 (s, 3H: CH₃); 1.41 (s, 9H: C(CH₃)₃); 1.78 (s, 3H: CH₃); 1.83 (s, 3H: CH₃); 1.88 (s, 1H: OH at position 1); 2.12 and 2.35 (2 dd, J=15 and 8, 1H each: CH₂ at position 14); 2.28 (s, 3H: COCH₃); 2.33 and 2.43 (2 dd, H at position 7'); 4.28 (limiting AB, J=8, 2H: CH₂ at position 20); 4.52 (d, J=6.5, 1H: H at position 3); 4.63 (mt, 1H: H at position 2'); 4.83 (mt, 1H: H at position 10); 5.06 (d, J=5, 1H: H at position 5); 5.30 (broad d, J=10, 1H: H at position 3'); 5.53 (d, J=10, 1H: CONH); 5.59 (d, J=6.5, 1H: H at position 2); 6.22 (broad t, J=8, 1H: H at position 13); 7.30 (t, J=7.5, 1H: H at the para position of the aromatic at position 3'); 7.37 (t, J=7.5, 2H: H at the meta position of the aromatic at position 3'); 7.44 (d, J=7.5, 2H: H at the ortho position of the aromatic at position 3'); 7.50 (t, J=7.5, 2H: OCOC₆H₅ H at the meta position); 7.61 (t, J=7.5, 1H: OCOC₆H₅ H at the para position); 8.09 (d, J=7.5, 2H: OCOC₆H₅ H at the ortho position).

EXAMPLE 4

1 mg of sodium hydride at 50% in oil is added to a solution of 10 mg of 4α-acetoxy-2α-benzoyloxy-5β,20-epoxy-1β,10β-dihydroxy-7α,9α-epoxy-11-taxen-13α-yl (2R,3S)-3-tert-butoxycarbonylamino-3-phenyl-2-triethylsilyloxypropionate in 0.1 cm³ of methyl iodide and 0.01 cm³ of anhydrous dimethylformamide under an argon atmosphere at a temperature in the region of 20° C. After 12 minutes at a temperature in the region of 20° C., the crude reaction mixture is purified by preparative thin-layer chromatography on silica [1 Merck preparative silica gel 60F$_{254}$ plate; 20×20 cm; thickness 0.5 mm; application of the crude reaction mixture], eluting with a methanol/dichloromethane (3–97 by volume) mixture. After elution of the zone corresponding to the desired product with a methanol/dichloromethane (15–85 by volume) mixture, filtration through cotton and then evaporation of the solvents under reduced pressure (2.7 kPa) at a temperature in the region of 40° C., 4.7 mg of 4α-acetoxy-2α-benzoyloxy-5β,20-epoxy-1β-hydroxy-10β-methoxy-7α,9α-epoxy-11-taxen-13α-yl (2R,3S)-3-tert-butoxycarbonylamino-3-phenyl-2-triethylsilyloxypropionate are obtained in the form of a white lacquer.

0.01 cm³ of hydrofluoric acid/triethylamine (3HF/Et₃N) complex is added dropwise to a solution of 4 mg of 4α-acetoxy-2α-benzoyloxy-5β,20-epoxy-1β-hydroxy-10β-methoxy-7α,9α-epoxy-11-taxen-13α-yl (2R,3S)-3-tert-butoxycarbonylamino-3-phenyl-2-triethylsilyloxypropionate in 0.1 cm³ of anhydrous dichloromethane maintained under an argon atmosphere at a temperature in the region of 20° C. After 35 minutes at a temperature in the region of 20° C., the crude reaction mixture is purified by preparative thin-layer chromatography on silica [1 Merck preparative silica gel 60F$_{254}$ plate; 20×20 cm; thickness 0.5 mm; application of the crude reaction mixture], eluting with a methanol/dichloromethane (4–96 by volume) mixture. After elution of the zone corresponding to the desired product with a methanol/dichloromethane (15–85 by volume) mixture, filtration through cotton and then evaporation of the solvents under reduced pressure (2.7 kPa) at a temperature in the region of 40° C., 3.3 mg of 4α-acetoxy-2α-benzoyloxy-5β,20-epoxy-1β-hydroxy-10β-methoxy-7α,9α-epoxy-11-taxen-13α-yl (2R,3S)-3-tert-butoxycarbonylamino-2-hydroxy-3-phenylpropionate are obtained in the form of a white lacquer, the characteristics of which are as follows:

¹H NMR spectrum (400 MHz; CDCl₃; at a temperature of 333° K, δ in ppm; coupling constants J in Hz): 1.17 (s, 3H: CH₃); 1.22 (s, 3H: CH₃); 1.41 (s, 9H: C(CH₃)₃); 1.67 (s, 3H: CH₃); 1.94 (s, 1H: OH at position 1); 2.00 (s, 3H: CH₃); 2.23 and 2.41 (2 dd, respectively J=15 and 8 and J=15 and 10, 1H each: CH₂ at position 14); from 2.20 to 2.40 (mt, 2H: CH₂ at position 6); 2.31 (s, 3H: COCH₃); 3.33 (s, 3H: OCH₃); 4.03 (unres. comp., 1H: OH at position 2'); 4.03 and 4.31 (2 d, J=7.5, 1H each: CH₂ at position 20); 4.13 (d, J=6.5, 1H: H at position 3); 4.29 (d, J=7, 1H: H at position 9); 4.67 (mt, 1H: H at position 2'); 4.77 (dd, J=8.5 and 5.5, 1H: H at position 7); 4.90 (d, J=7, 1H: H at position 10); 4.93 (broad s, 1H: H 5); 5.37 (broad d, J=10, 1H: H at position 3'); 5.61 (d, J=10, 1H: CONH); 5.81 (d, J=6.5, 1H: H at position 2); 6.06 (mt, 1H: H at position 13); 7.30 (t, J=7.5, 1H: H at the para position of the aromatic at position 3'); 7.38 (t, J=7.5, 2H: H at the meta position of the aromatic at position 3'); 7.46 (d, J=7.5, 2H: H at the ortho position of the aromatic at position 3'); 7.49 (t, J=7.5, 2H: OCOC₆H₅ H at the meta position); 7.63 (t, J=7.5, 1H: OCOC₆H₅ H at the para position); 8.13 (d, J=7.5, 2H: OCOC₆H₅ H at the ortho position).

EXAMPLE 5

4α-Acetoxy-2α-benzoyloxy-5β,20-epoxy-1β-hydroxy-7α,9α-oxa-10β-propanoyloxy-11-taxen-13α-yl (2R,3S)-3-tert-butoxycarbonylamino-3-phenyl-2-hydroxypropionate may be prepared in the following manner:

0.0053 cm³ of concentrated hydrochloric acid (36%, d=1.18) is added to a solution of 50 mg of 4α-acetoxy-2α- benzoyloxy-5β,20-epoxy-1β-hydroxy-7α,9α-oxa-10β-propanoyloxy-11-taxen-13α-yl (2R,4S,5R)-3-tert-butoxycarbonylamino-2-(4-methoxyphenyl)-4-phenyl-1,3-oxazolidine-5-carboxylate in 0.5 cm³ of ethyl acetate maintained at a temperature in the region of 20° C. After 2 hours at a temperature in the region of 20° C., the crude reaction mixture is purified by preparative thin-layer chromatography: 1 Merck preparative silica gel 60F₂₅₄ plate, 20×20 cm, thickness 1 mm, eluting with a methanol/dichloromethane (5–95 by volume) mixture. After elution of the zone corresponding to the desired product with a methanol/dichloromethane (15–85 by volume) mixture, filtration through sintered glass and then evaporation of the solvents under reduced pressure (2.7 kPa) at a temperature in the region of 40° C., 21 mg of 4α-acetoxy-2α-benzoyloxy-5β,20-epoxy-1β-hydroxy-7α,9α-oxa-10β-propanoyloxy-11-taxen-13α-yl (2R,3S )-3-tert-butoxycarbonylamino-3-phenyl-2-hydroxypropionate are obtained in the form of a white foam, the characteristics of which are as follows:

¹H NMR spectrum (400 MHz; CDCl₃; δ in ppm): 1.18 (t, J=7.5 Hz, 3H: CH₃ of the ethyl); 1.26 (s, 3H: CH₃); 1.33 (s, 3H: CH₃); 1.41 (s, 9H: C(CH₃)₃); 1.69 (s, 3H: CH₃); 1.92 (s, 3H: CH₃); 2.23 and from 2.25 to 2.50 (dd and mt respectively, J=16 and 8 Hz, 1H each: CH₂ 14); from 2.25 to 2.50 (mt, 4H: CH₂ 6 and OCOCH₂ ethyl); 2.33 (s, 3H: COCH₃); 3.97 (broad s, 1H: OH at position 2'); 4.03 and 4.31 (2 d, J=8 Hz, 1H each: CH₂20); 4.13 (d, J=6 Hz, 1H: 3); 4.68 (mt, 1H: H 2'); 4.84 (dd, J=8.5 and 5.5 Hz, 1H: H 7); 4.88 (d, J=6 Hz, 1H: H 9); 4.96 (broad s, 1H: H 5); 5.35 (broad d, J=10 Hz, 1H: H 3'); 5.58 (d, J=10 Hz, 1H: CONH); 5.69 and 5.85 (2 d, J=6 Hz, 1H each: H 2 and H 10); 6.05 (broad t, J=8 Hz, 1H: H 13); 7.31 (t, J=7.5 Hz, 1H: H at the para position of the aromatic at position 3'); 7.39 (t, J=7.5 Hz, 2H: H at the meta position of the aromatic at position 3'); 7.46 (d, J=7.5 Hz, 2H: H at the ortho position of the aromatic at position 3'); 7.50 (t, J=7.5 Hz, 2H: OCOC₆H₅ H meta); 7.53 (t, J=7.5 Hz, 1H: OCOC₆H₅ H para); 8.13 (d, J=7.5 Hz, 2H: OCOC₆H₅ H ortho).

4α-Acetoxy-2α-benzoyloxy-5β,20-epoxy-1β-hydroxy-7α,9α-oxa-10β-propanoyloxy-11-taxen-13α-yl (2R,4S,5R)-3-tert-butoxycarbonylamino-2-(4-methoxyphenyl)-4-phenyl-1,3-oxazolidine-5-carboxylate may be prepared in the following manner:

20 mg of 4-(N,N'-dimethylamino)pyridine and then 0.042 cm³ of propionic anhydride are added successively to a solution of 100 mg of 4α-acetoxy-2α-benzoyloxy-5β,20-epoxy-1β,10β-dihydroxy-7α,9α-oxa-11-taxen-13α-yl (2R,4S,5R)-3-tert-butoxycarbonylamino-2-(4-methoxyphenyl)-4-phenyl-1,3-oxazolidine-5-carboxylate in 1 cm³ of anhydrous pyridine maintained under an argon atmosphere at a temperature in the region of 20° C. After 2 hours at a temperature in the region of 20° C., the reaction mixture is diluted with 5 cm³ of dichloromethane and 2 cm³ of distilled water. After decantation, the organic phase is dried over magnesium sulphate, filtered through sintered glass and concentrated under reduced pressure (2.7 kPa) at a temperature in the region of 40° C. A colourless oil is thereby obtained which is purified by preparative thinlayer chromatography: 3 Merck preparative silica gel 60F₂₅₄ plates, 20×20 cm, thickness 1 mm, application in solution in a minimum volume of dichloromethane, eluting with a methanol/dichloromethane (5–95 by volume) mixture. After elution of the zone corresponding to the desired product with a methanol/dichloromethane (15–85 by volume) mixture, filtration through sintered glass and then evaporation of the solvents under reduced pressure (2.7 kPa) at a temperature in the region of 40° C., 51 mg of 4α-acetoxy-2α-benzoyloxy-5β,20-epoxy-1β-hydroxy-7α,9α-oxa-10β-propanoyloxy-11-taxen-13α-yl (2R,4S,5R)-3-tert-butoxycarbonylamino-2-(4-methoxyphenyl)-4-phenyl-1,3-oxazolidine-5-carboxylate are obtained in the form of a white foam, the characteristics of which are as follows:

¹H NMR spectrum (400 MHz; CDCl₃; δ ppm): 1.04 (t, J=7.5 Hz, 3H: CH₃ of the ethyl); 1.05 (s, 9H: C(CH₃)₃); 1.24 (s, 6H: CH₃); 1.63 (s, 3H: CH₃); 1.70 (s, 3H: CH₃); 1.80 (s, 3H: COCH₃); 2.10 and from 2.15 to 2.55 (dd and mt respectively, J=16 and 8 Hz, 1H each: CH₂ 14); from 2.15 to 2.55 (mt, 4H: CH₂ 6 and OCOCH₂ ethyl); 3.80 (s, 3H: ArOCH₃); 3.92 and 4.22 (2 d, J=8 Hz, 1H each: CH₂20); 4.02 (d, J=6 Hz, 1H: H 3); 4.62 (d, J=5 Hz, 1H: H 2'); 4.73 (dd, J=8 and 7.5 Hz, 1H: H 7); 4.78 (d, J=6 Hz, 1H: H 9); 4.88 (broad s, 1H: H 5); 5.35 (broad d, J=5 Hz, 1H: H 3'); 5.63 and 5.75 (2 d, J=6 Hz, 1H each: H 2 and H 10); 5.93 (broad t, J=8 Hz, 1H: H 13); 6.30 (broad s, 1H: H 5'); 6.89 (d, J=8.5 Hz, 2H: aromatic H at the ortho position of the OCH₃); from 7.25 to 7.50 (mt, 9H: aromatic H at position 3'-aromatic H at the meta position of the OCH₃ and OCOC₆H₅ H mecta); 7.58 (t, J=7.5 Hz, 1H: OCOC₆H₅ H para); 8.03 (d, J=7.5 Hz, 2H: OCOC₆H₅ H ortho).

4α-Acetoxy-2α-benzoyloxy-5β,20-epoxy-1β,10β-dihydroxy-7α,9α-oxa-11-taxen-13α-yl (2R,4S,5R)-3-tert-butoxycarbonylamino-2-(4-methoxyphenyl)-4-phenyl-1,3-oxazolidine-5-carboxylate may be prepared in the following manner:

60 mg of sodium borohydride are added to a solution of 1.1 g of 4α-acetoxy-2α-benzoyloxy-5β,20- epoxy-1β-hydroxy-9,10-dioxo-7β-trifluoromethane-sulphonate-11-taxen-13α-yl (2R,4S,5R)-3-tert-butoxycarbonylamino-2-(4-methoxyphenyl)-4-phenyl-1,3-oxazolidine-5-carboxylate in 30 cm³ of absolute ethanol maintained under an argon atmosphere at a temperature in the region of 0° C. After one hour at a temperature in the region of 0° C., the reaction mixture is diluted with 100 cm³ of ethyl acetate. The organic phase is washed with 50 cm³ of distilled water and then twice 25 cm³ of a saturated aqueous sodium chloride solution, dried over magnesium sulphate, filtered through sintered glass and concentrated under reduced pressure (2.7 kPa) at a temperature in the region of 40° C. 1.04 g of a pale yellow foam is thereby obtained, which product is purified by chromatography at atmospheric pressure on 50 g of silica (0.063–0.2 mm) contained in a column 2.5 cm in diameter, eluting with a methanol/dichloromethane (2–98 by volume) mixture, collecting 20 cm³ fractions. The fractions containing only the desired product are pooled and concentrated to dryness under reduced pressure (2.7 kPa) at 40° C. for 2 hours. 230 mg of 4α-acetoxy-2α-benzoyloxy-5β,20-epoxy-1β,10β-dihydroxy-7α,9α-oxa-11-taxen-13α-yl (2R,4S,5R)-3-tert-butoxycarbonylamino-2-(4-methoxyphenyl )-4-phenyl-1,3-oxazolidine-5-carboxylate are thereby obtained in the form of a white foam, the characteristics of which are as follows:

¹H NMR spectrum (400 MHz; CDCl₃; δ ppm): 1.05 (s, 9H: C(CH₃)₃); 1.10 (s, 3H: CH₃); 1.25 (s, 3H: CH₃); 1.58 (s, 3H: CH₃); 1.70 (s, 3H: CH₃); 1.85 (broad s, 3H: COCH₃); 2.10 and 2.22 (2 dd, J=16 and 8 Hz, 1H each: CH₂ 14); from 2.25 to 2.45 (mt, 2H: CH₂ 6); 3.82 (s, 3H: ArOCH₃); 3.93 and 4.23 (2 d, J=8 Hz, 1H each: CH₂ 20); 4.08 (d, J=6 Hz, 1H: H 3); 4.62 (d, J=5 Hz, 1H: H 2'); from 4.70 to 4.80 (mt, 2H: H 9 and H 10); 4.80 (dd, J=8.5 and 6 Hz, 1H: H 7); 4.88 (broad s, 1H: H5); 5.36 (unres. comp., 1H: H 3'); 5.75 (d, J=6 Hz 1H: H 2); 6.02 (broad t, J=8 Hz, 1H: H 13); 6.37 (broad unres. comp., 1H: H 5'); 6.95 (d, J=8.5 Hz, 2H: aromatic H at the ortho position of the OCH₃); from 7.25 to 7.55 (mt, 9H: aromatic H at position 3'-aromatic H at the meta position of the OCH$_3$ and OCOC$_6$H$_5$ H mecta); 7.65 (t, J=7.5 Hz, 1H: OCOC$_6$H$_5$ H para) [lacuna]7 (d, J=7.5 Hz, 2H: OCOC$_6$H$_5$ H ortho).

4α-Acetoxy-2α-benzoyloxy-5β,20-epoxy-1β-hydroxy-9, 10-dioxo-7β-trifluoromethanesulphonate-11-taxen-13α-yl (2R,4S,5R)-3-tert-butoxycarbonylamino-2-(4-methoxyphenyl)-4-phenyl-1,3-oxazolidine-5-carboxylate may be prepared in the following manner:

1.8 g of pyridinium chlorochromate are rapidly added to a suspension of 2.2 g of 4α-acetoxy-2α-benzoyloxy-5β,20-epoxy-1β,10β-dihydroxy-9-oxo-7β-trifluoromethanesulphonate-11-taxen-13α-yl (2R,4S,5R)-3-tert-butoxycarbonylamino-2-(4-methoxyphenyl)-4-phenyl-1,3-oxazolidine-5-carboxylate and 4.5 g of activated 4 Å molecular sieve in 10 cm$^3$ of anhydrous dichloromethane maintained under an argon atmosphere at a temperature in the region of 20° C. The reaction mixture is stirred for 17 hours at a temperature in the region of 20° C. and then filtered through Clarcel. The solid residue is rinsed with dichloromethane and then the filtrate is concentrated under reduced pressure (2.7 kPa) at a temperature in the region of 40° C. A brown foam is thereby obtained which is purified by chromatography at atmospheric pressure on 200 g of silica (0.063–0.2 mm) contained in a column 4 cm in diameter, eluting with a methanol/dichloromethane (0.5–99.5 by volume) mixture, collecting 20 cm$^3$fractions. The fractions containing only the desired product are pooled and concentrated to dryness under reduced pressure (2.7 kPa) at 40° C. for 2 h. 1.5 g of 4α-acetoxy-2α-benzoyloxy-5β,20-epoxy-1β-hydroxy-9,10-dioxo-7β-trifluoromethanesulphonate-11taxen-13α-yl (2R,4S,5R)-3-tert -butoxycarbonylamino-2-(4-methoxyphenyl)-4-phenyl-1,3-oxazolidine-5-carboxylate are thereby obtained in the form of a yellow foam, the characteristics of which are as follows:

$^1$H NMR spectrum (400 MHz; CDCl$_3$; δ in ppm): 1.07 (s, 9H: C(CH$_3$)$_3$); 1.20 (s, 3H: CH$_3$); 1.27 (s, 3H: CH$_3$); 1.58 (s, 3H: CH$_3$); 1.85 (s, 3H: CH$_3$); 1.94 (unres. comp., 3H: COCH$_3$); 2.13 and 2.27 (2 dd, J=16 and 8 Hz, 1H each: CH$_2$ 14); 2.13 and 2.82 (2 mts, 1H each: CH$_2$ 6); 3.66 (d, J=6.5 Hz, 1H: H 3); 3.84 (s, 3H: ArOCH$_3$); 4.11 and 4.31 (2 d, J=8 Hz, 1H each: CH$_2$ 20); 4.58 (d, J=5 Hz, 1H: H 2'); 4.81 (broad d, J=10 Hz, 1H: H 5); 5.18 (dd, J=10 and 7.5 Hz, 1H: H 7); 5.44 (unres. comp., 1H: H 3'); 5.77 (d, J=6.5 Hz, 1H: H 2); 6.11 (broad t, J=8 Hz, 1H: H 13); 6.40 (unres. comp., 1H: H 5'); 6.91 (d, J=8.5 Hz, 2H: aromatic H at the ortho position of the OCH$_3$); from 7.30 to 7.50 (mt, 7H: aromatic H at position 3'-aromatic H at the meta position of the OCH$_3$); 7.51 (t, J=7.5 Hz, 2H: OCOCH$_5$H meta); 7.66 (t, J=7.5 Hz, 1H: OCOC$_6$H$_5$ H para); 8.02 (d, J=7.5 Hz, 2H: OCOC$_6$H$_5$ H ortho).

The preparation of 4α-acetoxy-2α-benzoyloxy-5β,20-epoxy-1β,10β-dihydroxy-9-oxo-7β-trifluoromethanesulphonate-11-taxen-13α-yl (2R,4S,5R)-3-tertbutoxycarbonylamino-2-(4-methoxyphenyl)-4-phenyl-1,3-oxazolidine-5-carboxylate may be carried out, for example, according to the procedure described in Patent FR 9,408,198 (first filing of Apr. 7, 1994), hereby incorporated by reference.

EXAMPLE 6

4α-Acetoxy-2α-benzoyloxy-5β,20-epoxy-1β-hydroxy-10β-methoxyacetoxy-7α,9α-oxa-11-taxen-13α-yl (2R,3S)-3-tert-butoxycarbonylamino-3-phenyl-2-hydroxypropionate may be prepared in the following manner:

0.0053 cm$^3$ of concentrated hydrochloric acid (36%, d=1.18) is added to a solution of 30 mg of 4α-acetoxy-2α-benzoyloxy-5β,20-epoxy-1β-hydroxy-10β-methoxyacetoxy-7α,9α-oxa-11-taxen-13α-yl (2R,4S,5R)-3-tert-butoxycarbonylamino-2-(4-methoxyphenyl)-4-phenyl-1,3-oxazolidine-5-carboxylate in 1 cm$^3$ of ethyl acetate maintained at a temperature in the region of 20° C. After 45 minutes at a temperature in the region of 20° C., 0.002 cm$^3$ of concentrated hydrochloric acid is added. After 2 hours at a temperature in the region of 20° C., the crude reaction mixture is purified by applying to preparative thin-layer chromatography: 1 Merck preparative silica gel 60F$_{254}$ plate, 20×20 cm, thickness 0.5 mm, eluting with a methanol/dichloromethane (5–95 by volume) mixture. After elution of the zone corresponding to the desired product with a methanol/dichloromethane (15–85 by volume) mixture, filtration through sintered glass and then evaporation of the solvents under reduced pressure (2.7 kPa) at a temperature in the region of 40° C., 13 mg of 4α-acetoxy-2α-benzoyloxy-5β,20-epoxy-1β-hydroxy-10β-methoxyacetoxy-7α,9α-oxa-11-taxen-13α-yl (2R,3S)-3-tert-butoxycarbonylamino-3-phenyl-2-hydroxypropionate are obtained in the form of a white foam, the characteristics of which are as follows:

$^1$H NMR spectrum (400 MHz; CDCl$_3$; δ in ppm): 1.24 (s, 3H: CH$_3$); 1.31 (s, 3H: CH$_3$); 1.40 (s, 9H: C(CH$_3$)$_3$); 1.67 (s, 3H: CH$_3$); 1.86 (s, 3H: CH$_3$); 1.99 (s, 1H: OH at position 1); 2.20 and from 2.25 to 2.50 (dd and mt respectively, J=16 and 8 Hz, 1H each: CH$_2$ 14); from 2.25 to 2.50 (mt, 2H: CH$_2$ 6); 2.31 (s, 3H: COCH$_3$); 3.44 (s, 3H: OCH$_3$); 3.87 (broad s, 1H: OH at position 2'); 4.01 and 4.18 (2 d, J=8 Hz, 1H each: CH$_2$ 20); 4.04 and 4.11 (2 d, J=16.5 Hz, 1H each: OCOCH$_2$O); 4.10 (d, J=6 Hz, 1H: H 3); 4.64 (mt, 1H: H 2'); 4.80 (dd, J=8.5 and 5.5 Hz, 1H: H 7); 4.86 (d, J=6 Hz, 1H: H 9); 4.92 (broad s, 1H: H 5); 5.30 (broad d, J=10 Hz, 1H: H 3'); 5.53 (d, J=10 Hz, 1H: CONH); 5.74 and 5.80 (2 d, J=6 Hz, 1H each: H 2 and H 10); 6.01 (broad t, J=8 Hz, 1H: H 13); 7.30 (t, J=7.5 Hz, 1H: H at the para position of the aromatic at position 3'); 7.36 (t, J=7.5 Hz, 2H: H at the meta position of the aromatic at position 3'); 7.42 (d, J=7.5 Hz, 2H: H at the ortho position of the aromatic at position 3'); 7.47 (t, J=7.5 Hz, 2H: OCOC$_6$H$_5$ H mecta); 7.61 (t, J=7.5 Hz, 1H: OCOC$_6$H$_5$ H para); 8.11 (d, J=7.5 Hz, 2H: OCOC$_6$H$_5$ H ortho).

4α-Acetoxy-2α-benzoyloxy-5β,20-epoxy-1β-hydroxy-10β-methoxyacetoxy-7α,9α-oxa-11-taxen-13α-yl (2R,4S,5R)-3-tert-butoxycarbonylamino-2-(4-methoxyphenyl)-4-phenyl-1,3-oxazolidine-5-carboxylate may be prepared in the following manner:

0.093 cm$^3$ of n-butyllithium (in 1.6M solution in hexane) and then 8 minutes later 0.023 cm$^3$ of methoxyacetyl chloride are added to a solution of 90 mg of 4α-acetoxy-2α-benzoyloxy-5β,20-epoxy-1β,10β-dihydroxy-7α,9α-oxa-11-taxen-13α-yl (2R,4S,5R)-3-tert-butoxycarbonylamino-2-(4-methoxyphenyl)-4-phenyl-1,3-oxazolidine-5-carboxylate in 2 cm$^3$ of anhydrous tetrahydrofuran maintained under an argon atmosphere at a temperature in the region of −78° C. The cooling bath is removed and then the crude reaction mixture, after returning to a temperature in the region of 20° C., is purified by applying to preparative thin-layer chromatography: 2 Merck preparative silica gel 60F$_{254}$ plates, 20×20 cm, thickness 1 mm, eluting with a methanol/dichloromethane (5–95 by volume) mixture. After elution of the zone corresponding to the desired product with methanol/dichloromethane (15–85 by volume) mixture, filtration through sintered glass and then evaporation of the solvents under reduced pressure (2.7 kPa) at a temperature in the region of 40° C., 31 mg of 4α-acetoxy-2α-benzoyloxy-5β,20-epoxy-1β-hydroxy-10β-methoxyacetoxy-7α,9α-oxa-11-taxen-13α-yl (2R,4S,5R)-3-tert-butoxycarbonylamino-2-(4-methoxyphenyl)-4-phenyl- 1,3-oxazolidine-5-carboxylate are obtained in the form of a white foam, the characteristics of which are as follows:

$^1$H NMR spectrum (400 MHz; CDCl$_3$; δ ppm): 1.05 (s, 9H: C(CH$_3$)$_3$); 1.26 (s, 6H: CH$_3$); 1.64 (s, 3H: CH$_3$); 1.67 (unres. comp., 3H: CH$_3$); 1.78 (s, 3H: COCH$_3$); 2.10 and 2.21 (2 dd, J=16 and 8.5 Hz, 1H each: CH$_2$ 14); 2.29 (mt, 2H: CH$_2$ 6); 3.45 (s, 3H: OCH$_3$); 3.81 (s, 3H: ArOCH$_3$); 3.92 and 4.24 (2 d, J=8 Hz, 1H each: CH$_2$ 20); 4.00 (d, J=6 Hz, 1H: H 3); 4.03 and 4.10 (2 d, J=16 Hz, 1H each: OCOCH$_2$O); 4.62 (d, J=5 Hz, 1H: H 2'); 4.75 (dd, J=8 and 7.5 Hz, 1H: H 7); 4.82 (d, J=6 Hz, 1H: H 9); 4.85 (broad s, 1H: H 5); 5.34 (unres. comp. 1H: H 3'); 5.68 and 5.75 (2 d, J=6 Hz, 1H each: H 2 and H 10); 5.95 (mt, 1H: H 13); from 6.30 to 6.45 (very broad unres. comp., 1H: H 5'); 6.92 (d, J=8.5 Hz, 2H: aromatic H at the ortho position of the OCH$_3$); from 7.25 to 7.50 (mt, 9H: aromatic H at position 3'-aromatic H at the meta position of the OCH$_3$ and OCOC$_6$H$_5$ H mecta); 7.62 (t, J=7.5 Hz, 1H: OCOC$_6$H$_5$ H para); 8.06 (d, J=7.5 Hz, 2H: OCOC$_6$H$_5$ H ortho).

EXAMPLE 7

4α-Acetoxy-2α-benzoyloxy-5β,20-epoxy-1β-hydroxy-10β-dimethylaminocarbonyloxy-7α,9α-oxa-11-taxen-13α-yl (2R,3S)-3-tert-butoxycarbonylamino-3-phenyl-2-hydroxypropionate may be prepared in the following manner:

0.0043 cm$^3$ of concentrated hydrochloric acid (36%, d=1.18) is added to a solution of 40 mg of 4α-acetoxy-2α-benzoyloxy-5β,20-epoxy-1β-hydroxy-10β-dimethylaminocarbonyloxy-7α,9α-oxa-11-taxen-13α-yl (2R,4S,5R)-3-tert-butoxycarbonylamino-2-(4-methoxyphenyl)-4-phenyl-1,3-oxazolidine-5-carboxylate in 1 cm$^3$ of ethyl acetate maintained at a temperature in the region of 20° C. After 1.5 hours at a temperature in the region of 20° C., the crude reaction mixture is purified by applying to preparative thin-layer chromatography: 2 Merck preparative silica gel 60F$_{254}$ plates, 20×20 mm, thickness 0.5 mm, eluting with a methanol/dichloromethane (5–95 by volume) mixture. After elution of the zone corresponding to the desired product with a methanol/dichloromethane (15–85 by volume) mixture, filtration through sintered glass and then evaporation of the solvents under reduced pressure (2.7 kPa) at a temperature in the region of 40° C., 20 mg of 4α-acetoxy-2α-benzoyloxy-5β,20-epoxy-1β-hydroxy-10β-dimethylaminocarbonyloxy-7α,9α-oxa-11-taxen-13α-yl (2R,3S)-3-tert-butoxycarbonylamino-3-phenyl-2-hydroxypropionate are obtained in the form of a white foam, the characteristics of which are as follows:

$^1$H NMR spectrum (400 MHz; CDCl$_3$; δ in ppm): 1.24 (s, 3H: CH$_3$); 1.31 (s, 3H: CH$_3$); 1.40 (s, 9H: C(CH$_3$)$_3$); 1.69 (S,3H: CH$_3$); 1.91 (s, 1H: OH at position 1); 1.97 (s, 3H: CH$_3$); 2.22 and from 2.25 to 2.50 (dd and mt respectively, J=16 and 8 Hz, 1H each: CH$_2$ 14); from 2.25 to 2.50 (mt, 2H: CH$_2$ 6); 2.32 (s, 3H: COCH$_3$); 2.94 and 2.96 (2 s, 3H each: N(CH$_3$)$_2$); 3.96 (broad s, 1H: OH at position 2'); 4.03 and 4.31 (2 d, J=8 Hz, 1H each: CH$_2$ 20); 4.13 (d, J=6 Hz, 1H: H 3); 4.67 (mt, H 2'); 4.81 (dd, J=8.5 and 5.5 Hz, 1H: H 7); 4.91 (d, J=6 Hz, 1H: H 9); 4.95 (broad s, 1H: H 5); 5.24 (broad d, J=10 Hz, 1H: H 3'); 5.58 (d, J=10 Hz, 1H: CONH); 5.69 and 5.83 (2 d, J=6 Hz, 1H each: H 2 and H 10); 6.07 (broad t, J=8 Hz, 1H: H 13); 7.31 (t, J=7.5 Hz, 1H: H at the para position of the aromatic at position 3'); 7.39 (t, J=7.5 Hz, 2H: H at the meta position of the aromatic at position 3'); 7.46 (d, J=7.5 Hz, 2H: H at the ortho position of the aromatic at position 3'); 7.48 (t, J=7.5 Hz, 2H: OCOC$_6$H$_5$ H meta); 7.62 (t, J=7.5 Hz, 1H: OCOC$_6$H$_5$ H para); 8.13 (d, J=7.5 Hz, 2H: OCOC$_6$H$_5$ H ortho).

4α-Acetoxy-2α-benzoyloxy-5β,20-epoxy-1β-hydroxy-10β-dimethylaminocarbonyloxy-7α,9α-oxa-11-taxen-13α-yl (2R,4S,5R)-3-tert-butoxycarbonylamino-2(4-methoxyphenyl)-4-phenyl-1,3- oxazolidine-5-carboxylate may be prepared in the following manner:

0.103 cm$^3$ of n-butyllithium (in 1.6M solution in hexane) and then 5 minutes later 0.0253 cm$^3$ of dimethylaminocarbamoyl chloride are added to a solution of 100 mg of 4α-acetoxy-2α-benzoyloxy-5β,20-epoxy-1β, 10β-dihydroxy-7α,9α-oxa-11-taxen-13α-yl (2R,4S,5R)-3-tert-butoxycarbonylamino-2-(4-methoxyphenyl )-4-phenyl- 1,3-oxazolidine-5-carboxylate in 2 cm$^3$ of anhydrous tetrahydrofuran maintained under an argon atmosphere at a temperature in the region of −78° C. After 30 minutes at a temperature in the region of −78° C., the cooling bath is removed and then the cooled reaction mixture, after returning to a temperature in the region of 20° C., is diluted with 1 cm$^3$ of distilled water. After decantation, the aqueous phase is reextracted with 2 cm$^3$ of ethyl acetate. The pooled organic phases are dried over magnesium sulphate, filtered through sintered glass and concentrated under reduced pressure (2.7 kPa) at a temperature in the region of 40° C. 99 mg of a colourless lacquer are thereby obtained, which product is purified by preparative thin-layer chromatography: 2 Merck preparative silica gel 60F$_{254}$ plates, 20×20 cm, thickness 1 mm, application in solution in a minimum of dichloromethane, eluting with a methanol/dichloromethane (5–95 by volume) mixture. After elution of the zone corresponding to the desired product with methanol/dichloromethane (15–85 by volume) mixture, filtration through sintered glass and then evaporation of the solvents under reduced pressure (2.7 kPa) at a temperature in the region of 40° C., 43 mg of 4α-acetoxy-2α-benzoyloxy-5β, 20-epoxy-1β-hydroxy-10β-dimethylaminocarbonyloxy-7α, 9α-oxa-11-taxen-13α-yl (2R,4S,5R)-3-tert-butoxycarbonylamino-2-(4-methoxyphenyl)-4-phenyl-1,3-oxazolidine-5-carboxylate are obtained in the form of a white foam, the characteristics of which are as follows:

$^1$H NMR spectrum (400 MHz; CDCl$_3$; δ in ppm): 1.05 (s, 9H: C(CH$_3$)$_3$); 1.24 (s, 6H: CH$_3$); 1.61 (s, 3H: CH$_3$); 1.70 (s, 3H: CH$_3$); 1.81 (s, 1H: OH at position 1); 1.87 (s, 3H: COCH$_3$); 2.14 and from 2.15 to 2.35 (dd and mt respectively, J=16 and 8 Hz, 1H each: CH$_2$ 14); from 2.15 to 2.35 (mt, 2H: CH$_2$ 6); 2.92 (s, 6H: N(CH$_3$)$_2$); 3.80 (s, 3H: ArOCH$_3$); 3.92 and 4.23 (2 d, J=8 Hz, 1H each: CH$_2$ 20); 4.02 (d, J=6 Hz, 1H: H 3); 4.62 (d, J=5 Hz, 1H: H 2'); 4.71 (dd, J=8 and 7.5 Hz, 1H: H 7); 4.83 (d, J=6 Hz, 1H: H 9); 4.88 (broad s, 1H: H 5); 5.35 (broad d, J=5 Hz, 1H: H 3'); 5.68 and 5.77 (2 d, J=6 Hz, 1H: H 2 and H 10); 6.00 (broad t, J=8 Hz, 1H: H 13); 6.30 (s, 1H: H 5'); 6.92 (d, J=8.5 Hz, 2H: aromatic H at the ortho position of the OCH$_3$); from 7.25 to 7.50 (mt, 9H: aromatic H at position 3'-aromatic H at the meta position of the OCH$_3$ and OCOC$_6$H$_5$ H meta); 7.60 (t, J=7.5 Hz, 1H: OCOC$_6$H$_5$ H para); 8.05 (d, J=7.5 Hz, 2H: OCOC$_6$H$_5$ H ortho).

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various tissues and/or organs, comprising, without implied limitation, muscle, bone or connective tissue, the skin, brain, lungs, sex organs, the lymphatic or renal systems, mammary or blood cells, liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' rumour, Hodgkin's disease, melanoma, multiple myeloma, chronic lymphocytic leukaemia and acute or chronic granulocytic lymphoma. The new products according to the invention are especially useful for the treatment of cancer of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferably the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-toxic solvents. Preferably, the compositions take the form of aqueous solutions or suspensions, injectable solutions which can contain emulsifying agents, colourings, preservatives or stabilizers. However, the compositions may also be provided in the form of tablets, pills, powders or granules which can be administered via the oral route.

The choice of adjuvants or excipients may be determined by the solubility and the chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consist of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single dose contains from 0.01 to 1000 mg approximately of active product for parenteral administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphokines and cytokines such as interleukins, interferons ($\alpha$, $\beta$ or $\delta$) and TNF. Other chemotherapeutic agents which are useful in the treatment of disorders due to abnormal cell proliferation include, without implied limitation, alkylating agents, for instance nitrogen mustards such as mechlorethamine, cyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vindesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstilboestrol and ethynyloestradiol, antioestrogens such as tamoxifen, and androgens such as testosterone propionate and fluoxymesterone.

The doses used for carrying out the methods according to the invention are those which permit a prophylactic treatment or a maximum therapeutic response. The doses vary according to the administration form, the particular product selected and features distinctive to the subject to be treated. In general, the doses are those which are therapeutically effective for the treatment of disorders due to abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly stronger doses will be administered until an optimum effect is obtained. For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses are generally between 0.01 and 200 mg/kg. For intraperitoneal administration, the doses will generally be between 0.1 and 100 mg/kg, preferably between 0.5 and 50 mg/kg and still more specifically between 1 and 10 mg/kg. For intravenous administration, the doses are generally between 0.1 and 50 mg/kg, preferably between 0.1 and 5 mg/kg and still more specifically between 1 and 2 mg/kg. It is understood that, in order to choose the most suitable dosage, account should be taken of the administration route, the patient's weight, general state of health and age and all factors which may influence the efficacy of the treatment.

The example which follows illustrates a composition according to the invention.

EXAMPLE 40 mg of the product obtained in Example 1 are dissolved in 1 $cm^3$ of Emulphor EL 620 and 1 $cm^3$ of ethanol, and the solution is then diluted by adding 18 $cm^3$ of physiological saline.

The composition is administered by perfusion over 1 hour by introduction in physiological solution.

We claim:

1. A taxoid of the formula (I):

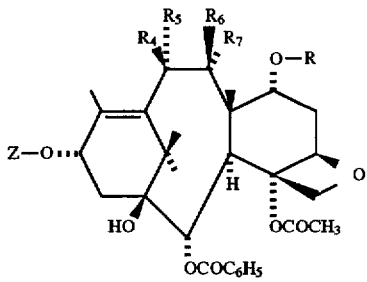

wherein:

Z represents a hydrogen atom or a radical of the formula (II):

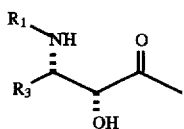

in which:

$R_1$ represents a benzoyl radical unsubstituted or substituted with at least one substituent selected from the group consisting of a halogen atom, an alkyl radical comprising 1 to 4 carbon atoms, an alkoxy radical comprising 1 to 4 carbon atoms, and a trifluoromethyl radical, a thenoyl radical, a furoyl radical, a radical $R_2$—O—CO— in which $R_2$ represents an alkyl radical comprising 1 to 8 carbon atoms, an alkenyl radical comprising 2 to 8 carbon atoms, an alkynyl radical comprising 3 to 8 carbon atoms, a cycloalkyl radical comprising 3 to 6 carbon atoms, a cycloalkenyl radical comprising 4 to 6carbon atoms, or a bicycloalkyl radical comprising 7 to 10 carbon atoms, these radicals being unsubstituted or substituted with at least one substituent selected from the group consisting of a halogen atom, a hydroxyl radical, an alkoxy radical comprising 1 to 4 carbon atoms, a dialkylamino radical in which each alkyl portion comprises 1 to 4 carbon atoms, a piperidino radical, a morpholino radical, a 1-piperazinyl radical (unsubstituted or substituted at position 4 with an alkyl radical comprising 1 to 4 carbon atoms or with a phenylalkyl radical in which the alkyl portion comprises 1 to 4 carbon atoms), a cycloalkyl radical comprising 3 to 6 carbon atoms, a cycloalkenyl radical comprising 4 to 6 carbon atoms, a phenyl radical (unsubstituted or substituted with at least one substituent selected from a halogen atom, an alkyl radical comprising 1 to 4 carbon atoms, and an alkoxy radical comprising 1 to 4 carbon atoms), a cyano radical, a carboxyl radical, and an alkoxycarbonyl radical in which the alkyl portion comprises 1 to 4 carbon atoms, a phenyl or α- or β-naphthyl radical unsubstituted or substituted with at least one substituent selected from the group consisting of a halogen atom, an alkyl radical comprising 1 to 4 carbon atoms, and an alkoxy radical comprising 1 to 4 carbon atoms, a 5-membered aromatic heterocyclic radical, or a saturated heterocyclic radical comprising 4 to 6 carbon atoms unsubstituted or substituted with at least one alkyl radical comprising 1 to 4 carbon atoms;

$R_3$ represents an unbranched or branched alkyl radical comprising 1 to 8 carbon atoms, an unbranched or branched alkenyl radical comprising 2 to 8 carbon atoms, an unbranched or branched alkynyl radical comprising 2 to 8 carbon atoms, a cycloalkyl radical comprising 3 to 6 carbon atoms, a cycloalkenyl radical comprising 4 to 6 carbon atoms, a phenyl or α- or β-naphthyl radical unsubstituted or substituted with at least one substituent selected from the group consisting of a halogen atom and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro, and trifluoromethyl radicals, or a 5-membered aromatic heterocycle comprising at least one identical or different hetero atom selected from the group consisting of nitrogen, oxygen and sulphur atoms, and unsubstituted or substituted with at least one identical or different substituent selected from the group consisting of a halogen atom and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl, and alkoxycarbonyl radicals, wherein for the substituents of the phenyl, α- or β-naphthyl, and aromatic heterocyclic radicals, the alkyl radicals and the alkyl portions of the other radicals comprise 1 to 4 carbon atoms, the alkenyl and alkynyl radicals comprise 2 to 8 carbon atoms, and the aryl radicals are phenyl or α- or β-naphthyl radicals; and either $R_4$ represents a hydrogen atom;

$R_6$ and $R_7$ together form a ketone function; and

R and $R_5$ together form a bond; or $R_4$ represents a hydrogen atom, a hydroxyl radical, an alkoxy radical comprising 1 to 6 carbon atoms in an unbranched or branched chain, an alkenyloxy radical comprising 3 to 6 carbon atoms in an unbranched or branched chain, an alkynyloxy radical comprising 3 to 6 carbon atoms in an unbranched or branched chain, a cycloalkyloxy radical comprising 3 to 6 carbon atoms, a cycloalkenyloxy radical comprising 3 to 6 carbon atoms, an alkanoyloxy radical in which the alkanoyl portion comprises 1 to 6 carbon atoms in an unbranched or branched chain, an aroyloxy radical in which the aryl portion comprises 6 to 10 carbon atoms, an alkenoyloxy radical in which the alkenoyl portion comprises 3 to 6 carbon atoms in an unbranched or branched chain, an alkynoyloxy radical in which the alkynoyl portion comprises 3 to 6 carbon atoms in an unbranched or branched chain, a cycloalkanoyloxy radical comprising 3 to 6 carbon atoms, an alkoxyacetyl radical in which the alkyl portion comprises 1 to 6 carbon atoms in an unbranched or branched chain, an alkylthioacetyl radical in which the alkyl portion comprises 1 to 6 carbon atoms in an unbranched or branched chain, an alkyloxycarbonyloxy radical in which the alkyl portion comprises 1 to 6 carbon atoms in an unbranched or branched chain, wherein these radicals are unsubstituted or substituted with at least one halogen atom, an alkoxy radical comprising 1 to 4 carbon atoms, an alkylthio radical comprising 1 to 4 carbon atoms, or a carboxyl radical, an alkyloxycarbonyl radical in which the alkyl portion comprises 1 to 4 carbon atoms, a cyano radical, a carbamoyl radical, an N-alkylcarbamoyl or N,N-dialkylcarbamoyl radical in which each alkyl portion comprises 1 to 4 carbon atoms or, with the nitrogen atom to which it is linked, forms a saturated 5- or 6-membered heterocyclic radical which can comprise a second hetero atom selected from the group consisting of oxygen, sulphur, and nitrogen atoms, and unsubstituted or substituted with an alkyl radical comprising 1 to 4 carbon atoms, a phenyl radical, or a phenylalkyl radical in which the alkyl portion comprises 1 to 4 carbon atoms, or alternatively $R_4$ represents a carbamoyloxy or alkylcarbamoyloxy radical in which the alkyl portion comprises 1 to 4 carbon atoms, a dialkylcarbamoyloxy radical in which each alkyl portion comprises 1 to 4 carbon atoms, a benzoyloxy radical, or a heterocyclylcarbonyloxy radical in which the heterocyclic portion comprises a 5- or 6-membered aromatic heterocycle comprising at least one hetero atom selected from the group consisting of oxygen, sulphur and nitrogen atoms;

$R_5$ represents a hydrogen atom; or $R_4$ and $R_5$ together form a ketone function;

$R_5$ represents a hydrogen atom; and

R and $R_7$ together form a bond.

2. The taxoid according to claim 1, wherein:

Z represents a hydrogen atom or a radical of the formula (II) in which $R_1$ represents a benzoyl radical or a radical $R_2$—O—CO— in which $R_2$ represents a tert-butyl radical, and $R_3$ represents an alkyl radical comprising 1 to 6 carbon atoms, an alkenyl radical comprising 2 to 6 carbon atoms, a cycloalkyl radical comprising 3 to 6 carbon atoms, a phenyl radical unsubstituted or substituted with at least one identical or different substituent selected from the group consisting of a halogen atom and alkyl, alkoxy, dialkylamino, acylamino, alkoxycarbonylamino, and trifluoromethyl radicals, a 2- or 3-furyl radical, a 2- or 3-thienyl radical, or a 2-, 4- or 5-thiazolyl radical; and either $R_4$ represents a hydrogen atom, $R_6$ and $R_7$ together form a ketone function, and R and $R_5$ together form a bond; or $R_4$ represents a hydroxyl radical, an alkoxy radical containing 1 to 6 carbon atoms, an alkanoyloxy radical comprising 1 to 6 carbon atoms, or an alkoxyacetyl radical in which the alkyl portion comprises 1 to 6 carbon atoms, $R_5$ represents a hydrogen atom, $R_6$ represents a hydrogen atom, and R and $R_7$ together form a bond; or $R_4$ and $R_5$ together form a ketone function, $R_6$ represents a hydrogen atom, and R and $R_7$ together form a bond.

3. The taxoid according to claim 1, wherein:

Z represents a hydrogen atom or a radical of the formula (II) wherein $R_1$ represents a benzoyl radical or a radical $R_2$—O—CO— in which $R_2$ represents a tert-butyl radical, and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical; and either $R_4$ represents a hydrogen atom, $R_6$ and $R_7$ together form a ketone function, and R and $R_5$ together form a bond; or $R_4$ represents a hydroxyl radical or a methoxy, acetoxy, or methoxyacetoxy radical, $R_5$ represents a hydrogen atom, $R_6$ represents a hydrogen atom, and R and $R_7$ together form a bond.

4. A process for preparing a taxoid according claim 1 in which Z is defined as in claim 1, and either $R_4$ represents a hydrogen atom, $R_6$ and $R_7$ together form a ketone function, and R and $R_5$ together form a bond, or $R_4$ represents a hydroxyl radical, $R_5$ represents a hydrogen atom, $R_6$ represents a hydrogen atom, and R and $R_7$ together form a bond;

the process comprising reacting a reducing agent with a compound of formula (III)

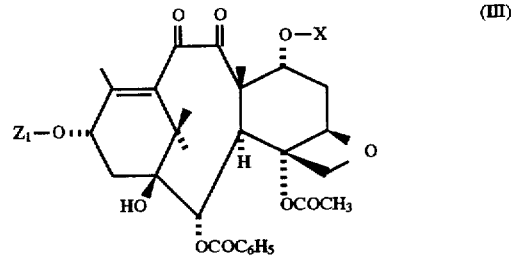

in which $Z_1$ represents a hydrogen atom, a group protecting the hydroxyl function, or a radical of the formula (IV):

in which $R_1$ and $R_3$ are defined as in claim 1 and $R_8$ represents a group protecting the hydroxyl function; and X represents, with the oxygen atom to which it is linked, a leaving group selected from alkylsulphonyl radicals comprising 1 to 4 carbon atoms unsubstituted or substituted with at least one halogen atom and arylsulphonyl radicals in which the aryl portion is a phenyl radical unsubstituted or substituted with at least one identical or different substituent selected from the group consisting of a halogen atom, an alkyl radical comprising 1 to 4 carbon atoms, a nitro radical, or a trifluoromethyl radical; to obtain a compound of the formula (V):

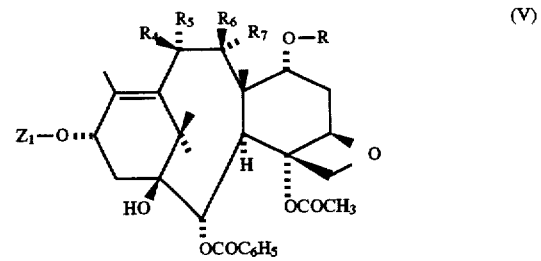

wherein $Z_1$, R, $R_4$, $R_5$, $R_6$ and $R_7$ are defined as above;

in the form of a mixture of a taxoid of formula (I) wherein $R_4$ represents a hydrogen atom, $R_6$ and $R_7$ together form a ketone function, and R and $R_5$ together form a bond and a taxoid of formula (I) wherein $R_4$ represents a hydroxyl radical, $R_5$ represents a hydrogen atom, $R_6$ represents a hydrogen atom, and R and $R_7$ together form a bond, followed by separating the mixture, and optionally replacing the protecting group represented by $Z_1$ or $R_8$ with a hydrogen atom.

5. The process according to claim 4, wherein the reducing agent is an aluminohydride or borohydride in the presence of an aliphatic alcohol comprising 1 to 4 carbon atoms and the reaction is carried out at a temperature between 0° and 50° C.

6. The process according to claim 4, wherein when the protecting group is a silylated radical, it is replaced by a hydrogen atom by using an inorganic acid in an aliphatic alcohol comprising 1 to 3 carbon atoms at a temperature between −10° and 20° C. or by using a hydrofluoric acid/triethylamine complex working in an inert organic solvent at a temperature of between 0° and 50° C.

7. A process for preparing a taxoid according to claim 1 in which:

Z is defined as in claim 11; and either $R_4$ represents an alkoxy radical comprising 1 to 6 carbon atoms in an unbranched or branched chain, an alkenyloxy radical comprising 3 to 6 carbon atoms in an unbranched or branched chain, an alkynyloxy radical comprising 3 to 6 carbon atoms in an unbranched or branched chain, a cycloalkyloxy radical comprising 3 to 6 carbon atoms, a cycloalkenyloxy radical comprising 3 to 6 carbon atoms, an alkanoyloxy radical in which the alkanoyl portion comprises 1 to 6 carbon atoms in an unbranched or branched chain, an alkenoyloxy radical in which the alkenoyl portion comprises 3 to 6 carbon atoms in an unbranched or branched chain, an alkynoyloxy radical in which the alkynoyl portion comprises 3 to 6 carbon atoms in an unbranched or branched chain, a cycloalkanoyloxy radical comprising 1 to 6 carbon atoms, an alkoxyacetyl radical in which the alkyl portion comprises 1 to 6 carbon atoms in an unbranched or branched chain, an alkylthioacetyl radical in which the alkyl portion comprises 1 to 6 carbon atoms in an unbranched or branched chain, or an alkyloxycarbonyloxy radical in which the alkyl portion comprises 1 to 6 carbon atoms in an unbranched or branched chain, these radicals unsubstituted or substituted with at least one substituent selected from the group consisting of a halogen atom, an alkoxy radical comprising 1 to 4 carbon atoms, an alkylthio radical comprising 1 to 4 carbon atoms, and a carboxyl radical, an alkyloxycarbonyl radical in which the alkyl portion comprises 1 to 4 carbon atoms, a cyano radical, a carbamoyl radical, an N-alkylcarbamoyl or N,N-dialkylcarbamoyl radical in which each alkyl portion comprises 1 to 4 carbon atoms or, with the nitrogen atom to which it is linked, forms a saturated 5- or 6-membered heterocyclic radical which can comprise a second hetero atom selected from the group consisting of oxygen, sulphur and nitrogen atoms, and unsubstituted or substituted with an alkyl radical comprising 1 to 4 carbon atoms, a phenyl radical, or a phenylalkyl radical in which the alkyl portion comprises 1 to 4 carbon atoms, or $R_4$ represents a carbamoyloxy radical, an alkylcarbamoyloxy radical in which the alkyl portion comprises 1 to 4 carbon atoms, a dialkylcarbamoyloxy radical in which each alkyl portion comprises 1 to 4 carbon atoms, a benzoyloxy radical, or a heterocyclylcarbonyloxy radical in which the heterocyclic portion represents a 5- or 6-membered aromatic heterocycle comprising at least one hetero atom selected from the group consisting of oxygen, sulphur and nitrogen atoms;

$R_5$ represents a hydrogen atom;

$R_6$ represents a hydrogen atom; and

R and $R_7$ together form a bond;

the process comprising reacting a compound of the formula (IX):

$$R'_4\text{—}Y \qquad (IX)$$

in which $R'_4$ is such that $R'_4$—O— is identical to $R_4$ defined above and Y represents a leaving group, with a compound of the formula (V):

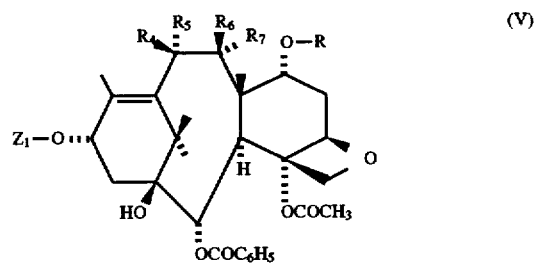

(V)

wherein $Z_1$ represents a hydrogen atom, a group protecting the hydroxyl function, or a radical of the formula (IV):

(IV)

in which $R_1$ and $R_3$ are defined as in claim 1 and $R_8$ represents a group protecting the hydroxyl function, $R_4$ represents a hydroxyl radical, $R_6$ represents a hydrogen atom, and R and $R_7$ together form a bond;

followed by replacing the protecting group represented by $Z_1$ or $R_8$ by a hydrogen atom by using an inorganic acid in an aliphatic alcohol comprising 1 to 3 carbon atoms at a temperature between −10° and 20° C. or by using a hydrofluoric acid/triethylamine complex working in an inert organic solvent at a temperature of between 0° and 50° C.

8. The process according to claim 7, wherein prior to the reaction of the compound of formula (IX) with the compound of formula (V), the hydroxyl function at position 10 may be metalated by using an alkali metal hydride, amide, or alkylide.

9. The process for preparing a taxoid according to claim 1 in which Z represents a radical of formula (II), $R_4$ and $R_5$ together form a ketone function, $R_6$ represents a hydrogen atom, and R and $R_7$ together form a bond; the process comprising oxidizing a compound of the formula (V):

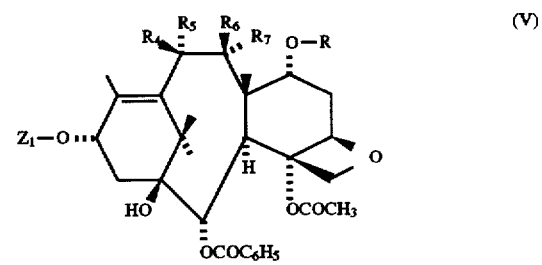

(V)

wherein $Z_1$ represents a hydrogen atom, a group protecting the hydroxyl function, or a radical of the formula (IV):

(IV)

in which $R_1$ and $R_3$ are defined as in claim 1 and $R_8$ represents a group protecting the hydroxyl function, $R_4$ represents a hydroxyl radical, $R_5$ represents a hydrogen atom, $R_6$ represents a hydrogen atom, and R and $R_7$ together form a bond; and then replacing the protecting group represented by $Z_1$ or $R_8$ by a hydrogen atom by using an inorganic acid in an aliphatic alcohol comprising 1 to 3 carbon atoms at a temperature between −10° and 20° C. or by using a hydrofluoric acid/triethylamine complex working in an inert organic solvent at a temperature of between 0° and 50° C.

10. The process according to claim 9, wherein the oxidation is carried out by using oxygen, ammonium peruthenate, manganese dioxide, copper acetate or pyridinium chlorochromate.

11. A process for preparing a taxoid according to claim 1, in which Z represents a radical of the formula (II), $R_4$, $R_5$ and $R_6$ each represent a hydrogen atom, and R and $R_7$ together form a bond;
the taxoid obtained from a compound of formula (V):

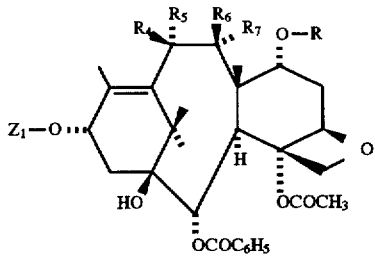

wherein $Z_1$ represents a hydrogen atom, a group protecting the hydroxyl function, or a radical of the formula (IV):

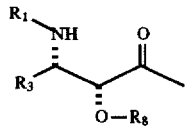

in which $R_1$ and $R_3$ are defined as in claim 1 and $R_8$ represents a group protecting the hydroxyl function, $R_4$ represents a hydroxyl radical, $R_5$ and $R_6$ each represent a hydrogen atom, and R and $R_7$ together form a bond;
by converting the hydroxyl radical represented by $R_4$ to a dithiocarbonate and then reducing the product obtained by using a trialkyltin hydride, which may be followed by replacing the protecting group represented by $Z_1$ or $R_8$ by a hydrogen atom by using an inorganic acid in an aliphatic alcohol comprising 1 to 3 carbon atoms at a temperature between −10° and 20° C. or by using a hydrofluoric acid/triethylamine complex working in an inert organic solvent at a temperature of between 0° and 50° C.

12. A process for preparing the taxoid of formula (I) according to claim 1, in which $R_4$, $R_5$, $R_6$, and $R_7$ are defined as in claim 1, wherein a taxoid of formula (I) in which Z is hydrogen is esterified by using an acid of the formula (X), or a derivative thereof:

wherein either $R_9$ represents a hydrogen atom and $R_{10}$ represents a group protecting the hydroxyl function, or $R_9$ and $R_{10}$ together form a saturated 5- or 6-membered heterocycle, followed by replacing the protecting groups by hydrogen atoms.

13. A pharmaceutical composition comprising at least one taxoid according to claim 1 in which Z represents a radical of formula (II) and at least one pharmaceutically-acceptable carrier.

14. The pharmaceutical composition according to claim 13 further comprising at least one compatible and pharmacologically active compound.

15. The taxoid according to claim 1, wherein the 5-membered aromatic heterocyclic radical represented by $R_1$ is a furyl or thienyl radical.

16. The process according to claim 5, wherein the borohydride is an alkali or alkaline-earth metal borohydride and the aliphatic alcohol is ethanol.

* * * * *

UNITED STATES PATENT AND TRADEMARK OFFICE
CERTIFICATE OF CORRECTION

PATENT NO. : 5,728,849
DATED : March 17, 1998
INVENTOR(S) : Hervé BOUCHARD et al.

It is certified that error appears in the above-identified patent and that said Letters Patent is hereby corrected as shown below:

Claim 1, column 25, line 37, "6carbon" should read --6 carbon--.

Claim 1, column 27, line 20, before "represents", "$R_5$" should read --$R_6$--.

Claim 4, column 27, line 64, after "according", insert --to--.

Claim 4, column 28, line 4, after "(III)", insert --:--.

Signed and Sealed this

Twenty-fifth Day of May, 1999

Attest:

Q. TODD DICKINSON

*Attesting Officer*　　　*Acting Commissioner of Patents and Trademarks*